US008036834B2

(12) United States Patent
Hood et al.

(10) Patent No.: US 8,036,834 B2
(45) Date of Patent: Oct. 11, 2011

(54) MULTIPARAMETER ANALYSIS FOR PREDICTIVE MEDICINE

(75) Inventors: Leroy Hood, Seattle, WA (US); Andrew F. Siegel, Shoreline, WA (US)

(73) Assignee: Institute for Systems Biology, Seattle, WA (US)

( * ) Notice: Subject to any disclaimer, the term of this patent is extended or adjusted under 35 U.S.C. 154(b) by 0 days.

(21) Appl. No.: 12/496,549

(22) Filed: Jul. 1, 2009

(65) Prior Publication Data

US 2010/0042329 A1 Feb. 18, 2010

Related U.S. Application Data

(63) Continuation of application No. 09/724,898, filed on Nov. 28, 2000, now Pat. No. 7,567,870.

(60) Provisional application No. 60/221,803, filed on Jul. 31, 2000, provisional application No. 60/226,328, filed on Aug. 17, 2000.

(51) Int. Cl.
*G06F 7/00* (2006.01)
(52) U.S. Cl. ............... 702/19; 702/20; 703/11; 707/700
(58) Field of Classification Search .......................... None
See application file for complete search history.

(56) References Cited

U.S. PATENT DOCUMENTS

| | | | |
|---|---|---|---|
| 5,814,445 A | 9/1998 | Belyavsky et al. |
| 6,020,135 A | 2/2000 | Levine et al. |
| 6,153,115 A | 11/2000 | Le et al. |
| 6,188,988 B1 | 2/2001 | Barry et al. |
| 6,194,217 B1 | 2/2001 | Matson |
| 6,203,987 B1 | 3/2001 | Friend et al. |
| 6,218,122 B1 | 4/2001 | Friend et al. |
| 6,251,601 B1 | 6/2001 | Bao et al. |
| 6,346,381 B1 | 2/2002 | Cohen et al. |
| 6,774,120 B1 | 8/2004 | Ferber |
| 7,343,247 B2 | 3/2008 | Hood et al. |
| 7,567,870 B1 | 7/2009 | Hood et al. |
| 2001/0018182 A1 | 8/2001 | Friend et al. |
| 2002/0095259 A1 | 7/2002 | Hood et al. |

FOREIGN PATENT DOCUMENTS

| | | |
|---|---|---|
| WO | WO/97/05553 | 2/1997 |
| WO | WO/98/53319 | 11/1998 |
| WO | WO/99/11822 | 3/1999 |
| WO | WO/99/57130 | 11/1999 |
| WO | WO/00/11208 | 3/2000 |
| WO | WO/00/70340 | 11/2000 |

OTHER PUBLICATIONS

Abe S., "Training of a fuzzy classifier with ellipsoidal regions by dynamic cluster generation," Second International Conference on Knowledge-Based Intelligent Electronic Systems pp. 126-131 (1998).
Aebersold et al., "Equipping scientists for the new biology," *Nat. Biotechnol.* 18:359 (2000).
Alon et al., "Broad patterns of gene expression revealed by clustering analysis of tumor and normal colon tissues probed by oligonucleotide arrays," *Proc. Natl. Acad. Sci. U.S.A.* 96:6745-6750 (1999).
Alper J., "Weighing DNA for fast genetic diagnosis," *Science* 279:2044-2045 (1998).
Anderson, An introduction to multivariate statistical analysis, second ed., chapter 6, pp. 195-243, Wiley, New York (1984).
Ben-dor et al., "Tissue classification with gene expression profiles," Proceedings of the Annual International Conference on Computational Molecular Biology, 4:54-64 (2000).
Burton and Harding, "Hydrophobic charge induction chromatography; salt independent protein adsorption and facile elution with aqueous buffers," *J. Chromatogr. A.* 814(1-2):71-81 (1998).
Claverie, "Computational methods for the identification of differential and coordinated gene expression," *Hum. Mol. Genet.* 8:1821-1832 (1999).
Cole et al., "The genetics of cancer—a 3D model," *Nat. Genet.* 21(1 Suppl):38-41 (1999).
Eichler et al., "Peptide, peptidomimetic, and organic synthetic combinatorial libraries," *Med. Res. Rev.* 15:481-496 (1995).
Ellington and Szostak, "In vitro selection of RNA molecules that bind specific ligands," *Nature* 346:818-822 (1990).
Emili and Cagney, "Large-scale functional analysis using peptide or protein arrays," *Nat. Biotechnol.* 18:393-397 (2000).
Famulouk M., "Oligonucleotide aptamers that recognize small molecules," *Curr. Opin Struct. Biol.* 9:324-329 (1999).
Famulok and Mayer, "Aptamers as tools in molecular biology and immunology," *Curr. Top. Microbiol. Immunol.* 243:123-136 (1999).
Fang et al., "Designing a novel molecular beacon for surface-immobilized DNA hybridization studies," *J. Am. Chem. Soc.* 121:2921-2922 (1999).
Fang et al., "Single and multiple molecular beacon probes for DNA hybridization studies on a silica glass surface," *SPIE* 3602:149-155 (1999).
Francis et al., "Combinatorial libraries of transition-metal complexes, catalysts and materials," *Curr. Opin. Chem. Biol.* 2:422-428 (1998).
Freund and Schapire, "A decision-theoretic generalization of on-line learning and an application to boosting," *J. Computer System Sciences* 55:119-139 (1997).
GeneExpress™: Integrated solutions for the drug discovery and development, www.genelogic.com printed Mar. 23, 2000.
"Gene Logic completes atlas of normal human gene expression," www.genelogic.com printed Mar. 23, 2000.

(Continued)

*Primary Examiner* — Mary Zeman
(74) *Attorney, Agent, or Firm* — Morrison & Foerster LLP

(57) ABSTRACT

The invention provides a method of determining a comparative expression profile in an individual by comparing the expression levels of a sample of molecules in a population of molecules in a specimen from the individual with a health-associated reference expression region of the sample of molecules, wherein expression levels within the health-associated reference expression region indicate a reference expression profile and wherein expression levels outside the health-associated reference expression region indicate a perturbed expression profile. The invention also provides methods of diagnosing a disease or a health state in an individual by comparing the expression level of a sample of molecules in a specimen from the individual with a health-associated reference expression region of the sample of molecules.

8 Claims, 7 Drawing Sheets

OTHER PUBLICATIONS

"Gene Logic and Fujisawa Pharmaceutical sign collaborative discovery research alliance; companies to identify gene expression profiles for diabetes therapeutics," www.genelogic.com printed Mar. 23, 2000.

Gold et al., "Diversity of oligonucleotide functions," *Annu. Rev. Biochem.* 64:763-797 (1995).

Golub et al., "Molecular classification of cancer: class discovery and class prediction by gene expression monitoring," *Science* 286:531-537 (1999).

Gygi et al., "Quantitative analysis of complex protein mixtures using isotope-coded affinity tags," *Nat. Biotechnol.* 17:994-999 (1999).

Hermann and Patel, "Adaptive recognition by nucleic acid aptamers," *Science* 287:820-825 (2000).

Hollstein et al., "p53 mutations in human cancers," *Science* 253:49-53 (1991).

Hughes et al., "Functional discovery via a compendium of expression profiles," *Cell* 102:109-126 (2000).

Jayasena S., "Aptamers: an emerging class of molecules that rival antibodies in diagnostics," *Clin. Chem.* 45:1628-1650 (1999).

Joyce G., "In vitro evolution of nucleic acids," *Curr. Opin. Struct. Biol.* 4:331-336 (1994).

Leethanakul, "Distinct pattern of expression of differentiation and growth-related genes in squamous cell carcinomas of the head and neck revealed by the use of laser capture microdissection and cDNA arrays," *Oncogene* 19:3220-3224 (2000).

Li and Breaker, "Deoxyribozymes: new players in the ancient game of biocatalysis," *Curr. Opin. in Struct. Biol.* 9:315-323 (1999).

Lorsch and Szostak, "Chance and necessity in the selection of nucleic acid catalysts," *Acc. Chem. Res.* 29:103-110 (1996).

Moler et al., "Analysis of molecular profile data using generative and discriminative methods," *Physiol. Genomics* 4(2):109-126 (2000).

Scherf et al., "A gene expression database for the molecular pharmacology of cancer," *Nat. Genet.* 24:236-244 (2000).

Sofia M., "Carbohydrate-based combinatorial libraries," *Mol. Divers.* 2:75-94 (1998).

Sutcliffe et al., "TOGA: an automated parsing technology for analyzing expression of nearly all genes," *Proc. Natl. Acad. Sci. U.S.A.* 97:1976-1981 (2000).

Suzuki et al., "Insulin resistance associated with creased levels of insulin-receptor messenger ribonucleic acid: evidence of a de novo mutation in the maternal allele," *J. Clin. Endocrinol. Metab.* 80:1214-1220 (1995).

Taira et al., "Human diabetes associated with a deletion of the tyrosine kinase domain of the insulin receptor," *Science* 245:63-66 (1989).

Tamayo et al., "Interpreting patterns of gene expression with self-organizing maps: methods and application to hematopoietic differentiation," *Proc. Natl. Acad. Sci. U.S.A.* 96:2907-2912 (1999).

Taylor S., "Lilly lecture: molecular mechanisms of insulin resistance," *Diabetes* 41:1473-1490 (1992).

Tietz Textbook Clinical Chemistry, 2nd ed., Burtis and Ashwood, eds., W.B. Saunders Co., Philadelphia, pp. 958-984, 992-997, 1053-1087, 1211-1228, 1320-1350, 1354-1372, 1743-1772, 1887-1913, and 2059-2066 (1994).

Tietz Textbook Clinical Chemistry, 3rd ed., Burtis and Ashwood, eds., W.B. Saunders Co., Philadelphia, Chapters 2 and 11-14, pp. 42-72 and 265-355 (1999).

Tokino and Nakamura, "The role of p53-target genes in human cancer," *Crit. Rev. Oncol. Hematol.* 33:1-6 (2000).

Tuerk and Gold, "Systematic evolution of ligands by exponential enrichment: RNA ligands to T4 DNA polymerase," *Science* 249:505-510 (1990).

Walt D., "Bead-based fiber-optic arrays," *Science* 287:451-452 (2000).

Wang X., Role of p53 and apoptosis in carcinogenesis, *Anticancer Res.* 19:4759-4771 (1999).

MULTIPARAMETER ANALYSIS FOR PREDICTIVE MEDICINE

This application is a continuation of U.S. Ser. No. 09/724,898, filed Nov. 28, 2000, which claims the benefit of priority of U.S. Provisional Application No. 60/221,803, filed Jul. 31, 2000, and U.S. Provisional Application No. 60/226,328, filed Aug. 17, 2000, each of which the entire contents are incorporated herein by reference.

BACKGROUND OF THE INVENTION

The present invention relates generally to methods of predictive medicine and more specifically to methods of determining expression profiles of an individual.

Every living organism utilizes genetic information in the form of discrete nucleotide sequences, called genes, to convey information for the proper development and function of the organism. Even simple organisms, such as bacteria, contain thousands of genes, and the number is many fold greater in complex organisms such as humans. Understanding the complexities of the development and functioning of living organisms requires knowledge of these genes.

For many years, scientists have searched for and identified a number of genes important in the development and function of living organisms. What was once a difficult and time consuming process has greatly accelerated in recent years due to advances in technology and directed projects aimed at identifying essentially all genetic information of an organism. The first draft of the human genome is now available, and more than 30 organisms have now had their entire genomes sequenced. The determination of the genome of additional organisms is currently being pursued.

One of the most ambitious of these genomic projects has been the Human Genome Project, with the goal of sequencing the entire human genome. The vast amount of genetic information available from the Human Genome Project provides a rich resource of potential targets for drug discovery as well as new diagnostic tools for medicine.

Although the determination of essentially all genes expressed in an organism is a rich resource of information, there remains the daunting task of applying this knowledge in a manner that is useful for practical medical applications. Perhaps 80,000 genes are expressed in human, and the analysis of such a large number of genes is complex. Moreover, in addition to the large number of genes, another layer of complexity arises from alternative splicing of mRNA and various modifications of proteins encoded by the genes. Furthermore, these gene expression patterns are expected to change when a individual has a disease. Information on gene expression patterns thus provides a basis for efficient and accurate diagnostic methods based on changes in gene expression in various diseases. The exploitation of genomics and proteomics information thus requires methods that can account for the large number of genes and complexity of gene expression patterns useful for medical applications. Fully exploiting genomics and proteomics information for medical applications requires methods that can accurately and efficiently monitor complex changes in gene expression patterns both at the mRNA and protein levels.

Thus, there exists a need for methods to efficiently diagnose a disease based on gene expression patterns in an individual. The present invention satisfies this need and provides related advantages as well.

SUMMARY OF THE INVENTION

The invention provides a method of determining a comparative expression profile in an individual by comparing the expression levels of a sample of molecules in a population of molecules in a specimen from the individual with a health-associated reference expression region of the sample of molecules, wherein expression levels within the health-associated reference expression region indicate a reference expression profile and wherein expression levels outside the health-associated reference expression region indicate a perturbed expression profile. The invention also provides methods of diagnosing a disease or a health state in an individual by comparing the expression level of a sample of molecules in a specimen from the individual with a health-associated reference expression region of the sample of molecules.

DETAILED DESCRIPTION OF THE INVENTION

Figure 1:
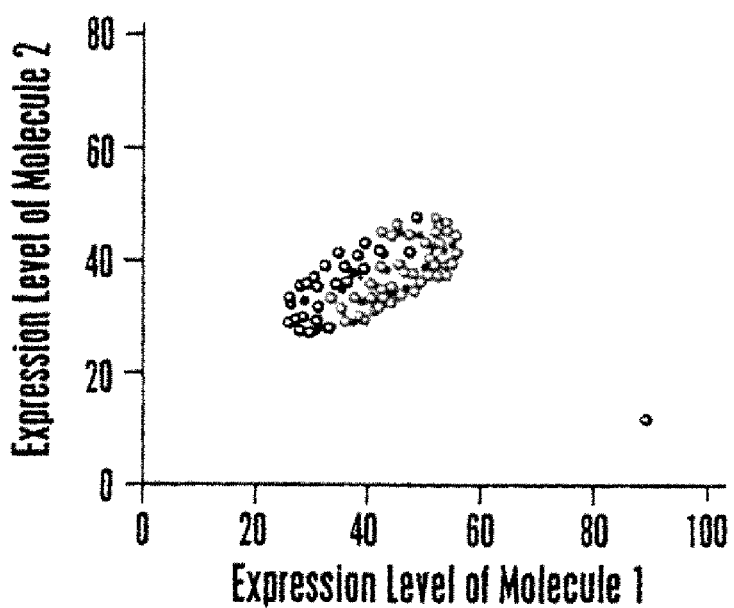
FIG. 1 shows a schematic diagram of a hypothetical health-associated reference expression region. The circles represent multidimensional coordinate points representative of the expression levels of two molecules in an individual. The expression levels are in arbitrary units. The top and bottom panels show a health-associated reference expression region of reference individuals in two-dimensional space as a region of coordinate points. The panels also show the coordinate points of two individuals that lie outside the health-associated reference expression region.
Figure 1:
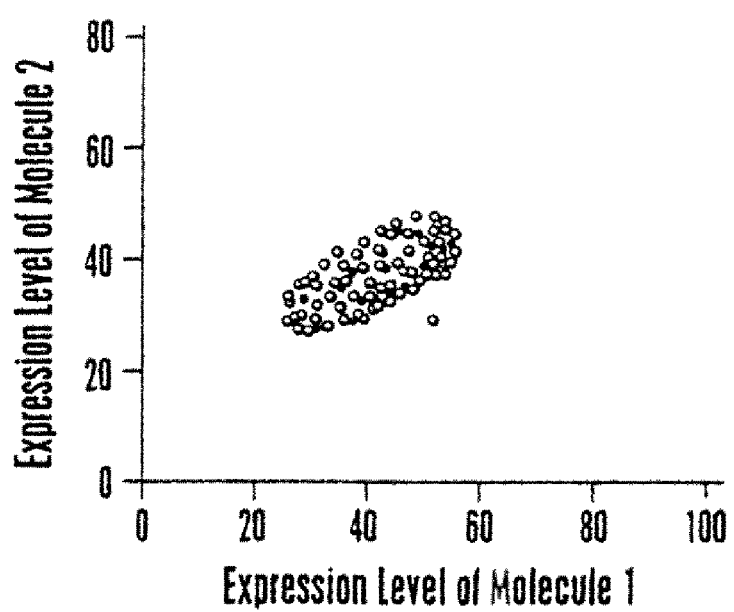

The invention provides a method of determining a comparative expression profile in an individual by comparing the expression levels of a sample of molecules in a population of molecules in a specimen from an individual with one or more health-associated reference expression regions of the sample of molecules. The specimen molecules can be nucleic acids, polypeptides, or small molecules.

The methods of the invention use statistically determined health-associated reference expression regions representing the expression levels of a sample of molecules in a population of reference individuals having a selected health state. For example, reference individuals can be normal, healthy individuals, and the expression levels in a population of healthy individuals can be determined for various molecules.

The methods of the invention can be used in a multiparameter analysis by measuring the expression levels of multiple molecules representative of the health state of an individual. For example, the expression levels of a sample of molecules in a specimen from an individual can be compared to a health-associated reference expression region representing the expression ranges of the corresponding individual molecules determined for the reference population of healthy individuals in a one-molecule-at-a-time analysis. In addition, the expression levels of the sample of molecules can be compared to the other molecules of the sample of molecules and to one or more health-associated reference expression regions in a multidimensional analysis. Such a comparison is useful for determining whether an individual has a health state similar to that of the reference population, for example, a healthy individual, or a health state that deviates from the reference population, for example, a disease state.

Expression levels of the specimen molecules that are within a health-associated reference expression region indicate a reference expression profile, whereas expression levels outside the health-associated reference expression region indicate a perturbed expression profile. The methods of the invention are advantageous in that they can be used to predict the health state of an individual by determining whether the individual has a reference expression profile indicative of a reference health state or a perturbed expression profile indicative of a potential disease state in the individual or of a predisposition to developing a disease. Moreover, the methods of the invention provide a multiparameter analysis of an individual's expression profile by measuring the expression level of multiple molecules, thus allowing the determination of an expression profile that is predictive of an individual's health, including the diagnosis of a disease, the prognosis of a disease, or estimating the course of a disease.

An individual who has a disease or is in early stages of developing a disease has characteristic changes in expression of molecules in a cell, including changes in gene expression that affect mRNA and protein expression, changes in modifications of molecules expressed in a cell, and/or changes in the expression of small molecules expressed in a cell or fluid sample from an individual. Changes in expression of molecules can reflect a disease state or a predisposition to developing a disease. Monitoring the expression level of molecules in a cell can thus be used to generate an expression profile, which can be correlated with the health of an individual. Such an expression profile is essentially a snapshot of the physiological state of the individual.

Although a particular disease can primarily affect one or a few systems, for example, cardiovascular disease affecting primarily the cardiovascular system, it is expected that a relatively homogeneous population of cells can provide a representative sampling of cells reflective of a variety of physiological systems, even if those cells are not directly associated with the particular disease. One such relatively homogeneous population of cells representative of a variety of physiological systems is white blood cells (WBCs), or subpopulations thereof. Accordingly, the methods of the invention can be conveniently performed with a specimen from an individual such as WBCs, which are readily accessible and can provide a window into many physiological systems, including cardiovascular, nervous, immune, gastrointestinal, endocrine, hepatic, lymphatic, neuromuscular, renal, respiratory, skeletal, and urogenital, metabolic systems, and the like, as disclosed herein.

For example, although a renal disease can affect primarily cells of the renal system, it is expected that WBCs, which are not directly involved in the renal disease, will nevertheless provide a window for observing physiological changes associated with the renal disease. The use of WBCs to monitor a variety of physiological changes is advantageous in that it obviates the need to obtain tissue specimens directly affected by the disease. Instead, readily accessible WBCs are used.

Furthermore, some white blood cells migrate through tissue and expand due to abnormalities such as inflammation, diseases such as cancer, autoimmune disease, or any disease that results in an immune response involving white blood cells. Expression of physiologically relevant genes in WBCs can be reset by control mechanisms in response to various pathologies. Accordingly, WBCs provide a conveniently accessible monitoring system for various pathologies and can therefore be advantageously used in methods of the invention for diagnosing a disease or predisposition to develop a disease, determining the prognosis of a disease, or estimating the course of a disease. The course of a disease includes the stage or severity of the disease, and can include the response of a patient to one or more treatments.

For example, macrophages, a subpopulation of white blood cells, respond to physiological changes, which in turn results in biochemical changes in the macrophages. Accordingly, macrophages can function as a window into the physiological changes that occur when an individual has a disease, a predisposition to developing a disease, or exhibits a particular course of a disease. Therefore, macrophages, or other WBCs or subpopulations thereof, provide a window into observing the network of physiological changes that can occur at various stages of disease development, including a pre-disease state indicative of a predisposition to developing a disease.

The methods of the invention can be used to diagnose a disease, determine the prognosis of a disease, or predict the course of a disease by obtaining a specimen from an individual, which can be a specimen that includes WBCs, and determining the health state of the individual. Exemplary diseases include, for example, cancer, including breast, prostate, ovarian, lung colorectal, hepatic, renal, leukemia, and lymphoma; cardiovascular diseases, including heart failure, hypertension and atherosclerosis; respiratory diseases; renal diseases; gastrointestinal diseases, including inflammatory bowel diseases such as Crohn's disease and ulcerative colitis; hepatic, gallbladder and bile duct diseases, including hepatitis and cirrhosis; hematologic diseases; metabolic diseases; endocrine and reproductive diseases, including diabetes; bone and bone mineral metabolism diseases; immune system diseases, including autoimmune diseases such as rheumatoid arthritis, lupus erythematosus, and other autoimmune diseases; musculoskeletal and connective tissue diseases, including arthritis; infectious diseases; and neurological diseases.

In addition, the methods of the invention directed to multiparameter analysis can also be used to identify one or more genetic defects. The methods of the invention can be particularly useful for diagnosing diseases resulting from multiple genetic defects and/or environmental factors. Accordingly, the methods of the invention can be useful in the diagnosis of polygenic diseases resulting from mutations in multiple genetic loci. Furthermore, a combination of genetic defects can be determined by methods of the invention, for example, a particular configuration of expression profiles can indicate the likely combination of genetic defects. Such information can be used to stratify a disease and can therefore be used to determine the stage of progression of a disease.

Furthermore, the relatively homogeneous population of WBCs can be further fractionated, for example, into lymphocytes such as T cells or B cells, granuolocytes, monocytes, macrophages, neutrophils, eosinophils, basophils, mast cells, and the like, and still be used as a representative sampling of cells useful for monitoring a variety of physiological systems. Even a single cell can be used as a representative specimen from an individual for use in methods of the invention.

The methods of the invention advantageously use a statistical analysis of the expression levels of molecules in a reference population of individuals to predetermine a health-associated reference expression region of molecules as they vary in the reference population. Such a health-associated reference expression region can be used to compare the expression level of molecules in an individual as a diagnostic method to determine the health state of the individual. The expression profile of an individual can be correlated with the health state of an individual, including whether an individual is healthy, has a disease, or has a predisposition to developing a disease. Such an expression profile is also useful in prognostic applications, including determining the prognosis of an individual who has a disease, selecting a therapy that is tailored to the physiological or genetic state of the individual, or estimating the course of a disease. Such information on the expression profile of an individual is thus applicable in both predictive medicine and preventive medicine.

The methods of the invention can be used as a tool for predictive medicine to diagnose a disease or diagnose the health state of an individual. Variations in expression of molecules such as DNA, mRNA, polypeptides or small molecules can be used to predict the health state of an individual. For example, an individual having expression levels of molecules that fall within a health-associated reference expression region is predicted to have a health state similar to the reference population. In the case where the reference population is healthy individuals, the individual is diagnosed as being healthy. An individual having molecules with expression levels outside the health-associated reference region has a perturbed health state, which can be correlated with a particular disease.

The methods of the invention can also be used to predict a predisposition to developing a disease or progression of a disease, for example, whether the disease is at an early stage or a late stage, by determining the expression levels of molecules that correlate with progress of the disease. Changes in expression levels of certain molecules are expected to occur during progression of a disease, and such changes in expression can therefore be used to predict the progress of a disease or a predisposition to developing a disease. Furthermore, once a correlation between expression levels and disease progression has been made, the methods of the invention can be used in preventive medicine by monitoring an individual for changes in expression levels that correlate with a predisposition to developing a disease or early stages of a disease. The individual can be then be treated prophylactically to prevent developing a disease or progression to a more severe form of the disease.

The methods of the invention use a statistically determined health-associated reference expression region of molecules indicative of expression levels of molecules in a population of reference individuals having a selected health state, thus accounting for natural variation in the expression of molecules in a population of reference individuals. The expression levels of molecules in a specimen from an individual can be compared to the statistically determined health-associated reference expression region to determine a comparative expression profile of the individual relative to the reference population. The determination of the reference expression region of a variety of molecules provides a basis for comparing any individual to determine if the individual has one or more molecules with aberrant expression or molecules having aberrant relative expression. Thus, the determination of a health-associated reference expression region for any number of molecules expressed in a cell provides a central repository of information, which can be accessed by a variety of means to determine a comparative expression profile of an individual. The analysis of an individual's expression profile can be advantageously performed using a computer, allowing direct or remote linking to a central repository of one or more health-associated reference expression regions generated by methods disclosed herein.

The methods of the invention can be used in direct diagnostic methods performed in a clinical laboratory or physician's office. Alternatively, the methods of the invention can be used in remote diagnostic methods in which the step of measuring the expression levels of molecules is physically separated from the step of comparing expression levels of molecules to a health-associated reference expression region. For example, the measurement of the expression levels of molecules can be performed by a health care professional or the patient at a remote location, such as a clinical laboratory, physician's office, or an individual's home, and the comparison step performed at a different location by conveniently interfacing the remote locations via a network such as the internet.

The methods of the invention can employ a variety of analytical systems to measure the expression levels of molecules in a specimen from an individual to be tested and from reference individuals for determining the health-associated reference expression intervals for various molecules. One convenient method for determining expression levels of molecules is to use a direct quantitation method such as the isotope-coded affinity tag (ICAT) method (Gygi et al., *Nature Biotechnol.* 17:994-999 (1999)). The ICAT method involves the comparison of a test sample and reference sample, which are differentially labeled with isotopes that can be distinguished using mass spectrometry, as described in more detail below. Other methods for measuring expression levels of molecules includes methods in which specimen molecules are first bound to a target such as an array based method. Molecules in a specimen from an individual are bound to target ligands on an array and detected to measure expression levels of the molecules, as described below. In addition to using an ICAT reagent that modifies polypeptides or fragments thereof having particular amino acids, polypeptide profiles, for example, a peptide map of a polypeptide where the peptides can be correlated with the polypeptide, can be used to measure the expression level of a polypeptide. Use of a peptide map to correlate with a polypeptide expression level can be used to obviate the labeling required for using the ICAT method, if desired.

As used herein, "expression level" refers to the amount of a molecule expressed in a cell that corresponds to the physiological state of the cell. The expression level of a molecule can be represented by the amount of messenger RNA (mRNA) encoded by a gene, the amount of polypeptide corresponding to a given amino acid sequence encoded by a gene, or the amount of biochemical forms of molecules expressed in a cell, including the amount of particular post-synthetic modifications of a molecule such as a polypeptide, nucleic acid or small molecule. As such, an expression level is intended to include a "gene expression level," a "cellular expression level," or both. The expression level can refer to an absolute amount of the molecule in a specimen or to a relative amount of the molecule. The expression level of a molecule can be determined relative to a control molecule in the specimen.

As used herein, "gene expression level" refers to the amount of a molecule encoded by a gene. The gene expression level of a molecule is intended to include the amount of mRNA, which is determined by the transcriptional activity of the gene encoding the mRNA, and the stability of the mRNA, which is determined by the half life of the mRNA. The gene expression level is also intended to include the amount of a polypeptide corresponding to a given amino acid sequence encoded by a gene. Accordingly, the expression level of a gene can correspond to the amount of mRNA transcribed from the gene, the amount of polypeptide encoded by the gene, or both.

As used herein, a "cellular expression level" refers to the amount of a biochemical form of a molecule expressed in a cell. Such differing biochemical forms are due to post-synthetic changes in the molecule, for example, processing or splicing of nucleic acids, postranslational modifications of polypeptides, or modifications of small molecules. Such post-translational modifications of polypeptides include, for example, phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. As such, a molecule such as a polypeptide having a specific amino acid sequence can exist in multiple biochemical forms, each of which can be quantitated to determine a cellular expression level. For example, a cellular expression level of a molecule can be the amount of a particular form of the molecule such as the phosphorylated form of a polypeptide. Furthermore, multiple forms of the molecule can exist, for example, based on the phosphorylation state at different sites on the same polypeptide. The amount of each of these different biochemical forms is intended to be included in the meaning of a cellular expression level. Furthermore, a polypeptide itself can be measured for expression levels or, if desired, peptide fragments that are correlated with a polypeptide, for example, peptides of a peptide map, can be measured. As such, analysis of a sufficient number of peptides to correlate with a polypeptide functions as a polypeptide profile and can be used to correlate the expression level of a polypeptide molecule.

A biochemical form of a small molecule can include, for example, a modification of a sugar, including glucose or modifications thereof such as glucose 1-phosphate, glucose 6-phosphate, glucose 1,6-diphosphate, glucuronic acid, glucosaine, N-acetylglucoseamine, and the like. Other exemplary small molecules include other sugars and carbohydrates, including lactose, maltose, galactose, fructose, and xylose, derivatives thereof, and metabolites thereof such as lactate and pyruvate; salts, ions, atoms and metals such as sodium, potassium, chloride, calcium, bicarbonate/$CO_2$, chromium, iron, magnesium, manganese, phosphate, molybdenum, selenium, zinc, copper, cobolt, fluoride, nickel, vanadium, silicon, arsenic, boron and the like; amino acids; lipids, including cholesterol, triglyceride and fatty acids; neurotransmitters and metabolites thereof such as acetylcholine, dopamine, norepinephrine, epinephrine, serotonin, γ-aminobutyrate, metanephrine, normetanephrine, vanillylmandelic acid, 3-methoxy-4-hydroxyphenylglycol, homovanillic acid, 5-hydroxyindoleacetic acid. The small molecules can be intermediates or products of metabolic or synthetic pathways. Changes in the expression of small molecules occurs in various diseases and can be used to predict a disease or susceptibility to a disease. For example, an iron deficiency is indicative of certain diseases while an iron excess is indicative of different diseases. Thus, the level of iron in an individual can be used, for example, in combination with other molecules, including other small molecules, nucleic acids, or polypeptides, to determine the health state of an individual.

As used herein, an "expression profile" refers to a characteristic representation of the expression level of at least two molecules in a specimen such as a cell or tissue. The determination of an expression profile in a specimen from an individual is representative of the expression state of the individual. An expression profile reflects the gene expression level and/or cellular expression level of at least two molecules in a specimen such as a cell or tissue.

An expression profile can be related to the expression levels of multiple molecules, allowing multiparameter analysis and correlation with the health state of an individual. For example, the expression profile of an individual will be perturbed by exposure to environmental or internal stimuli that result in physiological changes such as exposure to compounds or other environmental challenges or internal changes due to disease or other conditions that alter physiology. Such changes in expression can be readily be measured, as disclosed herein, and correlated with the physiological changes. In the case where particular molecules exhibit such variation in expression that they cannot be correlated with the corresponding physiological change in the individual, such molecules can be discarded from the analysis.

As used herein, a "gene expression profile" refers to a characteristic representation of the gene expression level in a specimen such as a cell or tissue. The determination of a gene expression profile in a specimen from an individual is representative of the gene expression state of the individual. A gene expression profile reflects the expression of messenger RNA or polypeptide encoded by one or more genes in a cell or tissue.

As used herein, a "cellular expression profile" refers to a characteristic representation of the cellular expression level in a specimen such as a cell or tissue. The determination of a cellular expression profile in a specimen from an individual is representative of the cellular expression state of the individual. A cellular expression profile reflects the expression levels of biochemical forms of messenger RNA or polypeptides encoded by one or more genes in a cell or tissue, or by small molecules expressed in blood, a cell or tissue. The cellular expression profile can also reflect ratios of different types of cells. Accordingly, if desired, a specimen can be optionally analyzed in a cell sorter to determine if cell ratios have changed from a reference population. Such a cell sorting analysis can be performed to enrich for a subpopulation of cells, for example, a subpopulation of WBCs isolated with ligands specific for cell surface antigens, as disclosed herein. In addition, information on cell ratios can be combined with expression profiles determined by methods of the invention to provide additional information useful in diagnosing a disease, determining the prognosis of a disease, or predicting the course of a disease.

As used herein, a "comparative expression profile" refers to an expression profile that reflects the expression levels of molecules relative to a health-associated reference expression region. A comparative expression profile thus reflects the expression level of two or more molecules in an individual relative to the reference expression levels for the respective molecules, that is, whether the expression level of a molecule is within a health-associated reference expression region or whether the expression level of the molecule is outside a health-associated reference expression region.

As used herein, a "region," when used in reference to expression levels of molecules, refers to a region of multidimensional space classified using one or more statistical methods. The region represents a classification of expression levels that is representative of a health state and is diagnostically useful for determining the health state of an individual. One or more statistical methods, as disclosed herein, can be used to define a region of multidimensional space. Exemplary statistical methods include, for example, discriminant analysis, classification analysis, cluster analysis, analysis of variance (ANOVA), regression analysis, regression trees, decision trees, nearest neighbor algorithms, principal components, factor analysis, multidimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis using prior probability distributions.

As used herein, a "health-associated reference expression region" refers to a region of multidimensional space that is representative of the expression levels of a sample of molecules in a population of reference individuals. A health-associated reference expression region can be used in a one-molecule-at-a-time analysis, in which the expression levels of individual molecules are compared to the expression levels of the corresponding molecules in a population of reference individuals. When a one-molecule-at-a-time analysis is applied, the expression level of an individual molecule is compared to a health-associated reference expression region that is a health-associated reference expression interval. In multidimensional analysis, the expression levels of individual molecules in a sample of molecules can be compared to other molecules in the sample of molecules to determine a multidimensional coordinate point representative of the expression levels of a sample of molecules in a population.

As used herein, a "multidimensional coordinate point" refers to a coordinate defined by "n" parameters, where n is the number of molecules in a sample of molecules and each parameter is the level of expression of a molecule in the sample. Accordingly, a multidimensional coordinate point representative of the expression levels of two molecules is defined by two parameters corresponding to the expression levels of the two molecules (see FIG. 1). Similarly, a multidimensional coordinate point representative of the expression levels of three molecules is defined by three parameters corresponding to the expression levels of the three molecules (see FIG. 2). A multidimensional coordinate point representative of the expression levels of n molecules is defined by n parameters corresponding to the expression levels of n molecules. Accordingly, multidimensional coordinate points for a group of individuals such as a reference population is found in n-dimensional shape space. Multidimensional coordinate points are determined for a sample of molecules in individuals of a reference population, and the multidimensional coordinate points can be used to determine a health-associated reference expression region for the reference population.

As used herein, a "health-associated reference expression interval" refers to a statistically determined range of expression levels of a molecule in a population of molecules such as mRNA, polypeptide, small molecules, or biochemical forms of a molecule that is determined by measuring the expression level of the molecule in a statistically representative population of reference individuals. As used herein, a "reference individual" refers to an individual selected for comparison using defined criteria. One skilled in the art can readily determine criteria suitable for inclusion of an individual as a reference individual for a particular application of methods of the invention, as described below. As used herein, a "reference population" refers to a group of two or more reference individuals.

Any relevant criteria can be used for identifying a suitable reference individual for a desired comparison. For example, a reference individual can be a healthy individual who is in good health and essentially disease free. One skilled in the art can readily determine if an individual is in good health based on subjective feelings of well being of the individual and objective signs of disease in an individual. Other criteria can include gender, ethnic background, presence of disease, or any criteria useful for comparing the health state of an individual.

Once reference criteria have been identified, for example, the reference criteria of healthy individuals, a population of individuals is selected as reference individuals to determine a health-associated reference region of molecules expressed in the individuals. One skilled in the art can readily determine desired criteria for the reference population and select individuals fitting the desired criteria. In one embodiment, the reference population is healthy individuals. A particularly useful reference population can be one or more families having members who are healthy and have a family history indicating no known genetic diseases. Such a reference population of family members can also be useful for distinguishing those molecules having a statistically reproducible expression interval from those molecules having such variability in expression that no relevant health-associated reference expression region can be determined.

An individual expresses a given molecule at a given level that is characteristic of the genotype and physiological state of the individual, including his or her health state. An individual also expresses a set of molecules at a combination of levels whose joint distribution is characteristic of the genotype and physiological state of the individual, including his or her health state. Due to genetic variation, healthy individuals will express variable levels of a given gene depending on the genotype of each individual. Accordingly, these variable expression levels of a given gene in a population of individuals correspond to a range of expression levels characteristic of the health state of the individuals. Such an expression range can be predetermined by sampling a sufficient number of reference individuals and determining the corresponding statistically useful health-associated reference expression intervals found in these individuals.

An individual can also be characterized with respect to a set of molecules having a joint distribution characteristic of the genotype and physiological state of the individual. The expression levels of such a set of molecules can be used to define a multidimensional coordinate point, which can be compared to one or more health-associated reference expression regions to determine if the individual has a reference health state or a perturbed health state.

In addition to genetic variation, the expression level of molecules can also vary due to the physiological state of the individual. Even in individuals considered to be healthy, the expression levels of molecules can vary depending on the individual's physiological state. For example, the expression level of molecules in an individual can vary with diet, drug intake, age, gender, and physiological state such as exercise, resting or sleeping. Therefore, if desired, a reference individual can be selected based on criteria that account for such variability, for example, by controlling diet by collecting specimens from individuals after 12 hours of fasting or restricting drug intake for an appropriate period of time prior to obtaining a specimen.

A health-associated reference expression region is a region of multidimensional space determined by the expression levels of a sample of molecules, and the boundaries of the region represent the perturbation limit, outside of which indicates that an individual has a perturbed expression profile that lies outside the statistical boundaries of the reference population. For example, in a one-molecule-at-a-time analysis, the upper and lower boundaries of a health-associated reference expression interval represent the perturbation limit, above or below which indicates that an individual has perturbed expression of a molecule that lies outside the statistical boundaries of the reference population. An individual with perturbed expression of a molecule, with a level of expression that lies outside the interval determined from reference individuals, potentially has a disease state. The greater the number of molecules that are expressed at levels outside a health-associated reference expression interval, the greater the likelihood that such perturbations are associated with a disease state. Similarly, the greater the deviation of a multidimensional coordinate point of an individual from a health-associated reference expression region, the greater the likelihood that such perturbations are associated with a disease state.

As used herein, a "reference expression level" refers to the expression level of a molecule that is correlated with a health-associated reference expression interval. One skilled in the art can readily determine a reference expression level by determining the expression level of a molecule in a reference specimen relative to a health-associated reference expression interval, for example, using appropriate standards, as described below. A reference expression level can be any level suitable for measuring and comparing expression levels of molecules between different specimens, although the reference expression level will generally be within the health-associated reference expression interval. In one embodiment, the reference expression level can be an average of the health-associated reference expression interval (see below).

As used herein, a "sample," when used in reference to molecules in a population, refers to a group of molecules in a population having expression levels that are predictive of the health state of an individual. The sample of molecules in the population includes molecules that exhibit disease-specific changes in expression as well as molecules having altered expression in a disease but which are not specific to a particular disease. A sample of molecules can also be a set of molecules with expression levels having a joint distribution characteristic of a health state of an individual. In such a case, the expression levels of individual molecules can fall within a reference expression interval but still be considered a member of a sample of molecules because the relative expression of molecules is outside a health-associated reference expression region (see below and FIG. 1). Accordingly, a molecule having an expression level within a health-associated reference expression interval can be included in a sample of molecules if the expression of that molecule relative to another sample molecule can be correlated with a health state.

A sample of molecules in a population that is predictive of the health state of an individual is a group of molecules having statistically determinable expression ranges in a given reference population. As used herein, a sample of molecules in a population can exclude molecules exhibiting expression levels that are so variable in a reference population that no statistically useful health-associated reference expression interval can be determined. Additionally, a sample of molecules, as used herein, can specifically exclude molecules that do not exhibit changes in expression with various health states since such molecules would not be predictive of the health state of an individual.

One skilled in the art can readily determine molecules that do not exhibit changes in expression with various health states or that are so variable in a reference population that no statistically useful health-associated reference expression region can be determined. For example, to determine molecules having variable expression levels unsuitable for obtaining statistically useful health-associated reference expression region, expression levels of molecules in a reference population can be examined for variability, and those exhibiting variability in expression insufficient for determining a statistically useful health-associated reference expression region can be disregarded. A reference population particularly useful for determining molecules with variable expression is one containing family members such as healthy family members. Due to the similar genetic background of family members, such a reference population can be used to identify molecules having variable expression since a reference population of related, healthy family members is expected to exhibit limited genetic variability and, therefore, observed variable expression is likely associated with molecules that exhibit natural variability in expression, which can be disregarded if the variability precludes obtaining statistically useful expression intervals. Such a reference population can be useful to identify molecules in the same or other reference populations that have variable expression such that they are preferably excluded from analysis of an expression profile of a sample.

As used herein, a "reference expression profile" refers to a characteristic representation of the expression state of a sample of molecules in a population of molecules in a specimen that falls within a health-associated reference expression region. As such, a reference expression profile indicates that the expression levels determined for a sample of molecules in a specimen from an individual lie within the predetermined expression levels for those sample molecules or within a health-associated reference expression region. An individual having a reference expression profile therefore has a health state substantially the same as the reference population.

As used herein, a "perturbed expression profile" refers to a characteristic representation of the expression state of a sample of molecules of a population that falls outside a health-associated reference expression region. As such, a perturbed expression profile indicates that the expression level determined for the sample molecules lies outside the health-associated reference expression intervals for the sample molecules or that multidimensional coordinate points representative of the sample of molecules lie outside a health-associated reference expression region. An expression level of a molecule that is below a lower perturbation limit or above an upper perturbation limit or multidimensional coordinate points that lie outside of a health-associated reference expression region indicates that an individual potentially has a disease state. The greater the number of molecules having levels outside the health-associated reference expression intervals of a healthy population, that is, above or below the perturbation limits, or the further the deviation of the multidimensional coordinate points from a health-associated reference expression region, the more likely such an individual has a disease state. The determination of a perturbed expression profile can be useful even in those individuals in which the perturbed expression profile is not associated with a disease state since such a perturbed expression state can be used as a prognostic indicator for individuals predisposed to developing a disease state.

As used herein, a "health state" refers to the medical condition of an individual. As used herein, a "reference health state" or "reference state" refers to the health state of an individual having a reference expression profile and is considered to have substantially the same or a similar health state as a reference population.

As used herein, a "perturbed health state" refers to the health state of an individual having a perturbed expression profile. Such an individual having a perturbed health state therefore has a sample of molecules in a population of molecules with expression levels that lie outside the health-associated reference expression region for those sample molecules. It is understood that a person having a perturbed health state relative to a healthy reference population can appear to be healthy in that the individual does not present any signs or symptoms of a disease. However, such a person having a perturbed health state can be predisposed to developing a disease. An individual having a perturbed health state also includes an individual who has a disease state. As used herein, a "disease state" refers to the health state of an individual who has a disease or has signs or symptoms associated with a disease. One skilled in the art can readily determine if an individual has signs or symptoms associated with a particular disease. Moreover, one skilled in the art can also readily determine whether an individual has signs or symptoms that are recognizable as lying outside the condition of a healthy individual.

As used herein, the term "specimen" is intended to mean any biological fluid, cell, tissue, organ or portion thereof, that includes one or more different molecules such as nucleic acids, polypeptides, or small molecules. The specimens used in methods of the invention contain nucleic acids, polypeptides, small molecules or biochemical forms of polypeptides that are representative of the expression level of molecules in the individual. The term includes specimens present in an individual as well as specimens obtained or derived from the individual. For example, a specimen can be a tissue section obtained by biopsy, or cells that are placed in or adapted to tissue culture. A specimen can also be a biological fluid specimen such as blood, urine or saliva. A specimen can be further fractionated, if desired, to a fraction containing particular cell types. For example, a blood specimen can be fractionated into serum or into fractions containing particular types of blood cells such as red blood cells or white blood cells (leukocytes). A particularly useful specimen for use in the invention is white blood cells since these cells can be correlated with a variety of physiological states, as disclosed herein. If desired, a specimen can be a combination of specimens from an individual such as a combination of a tissue and fluid specimen, and the like.

As used herein, a "target" means a collection of two or more ligands. A target of the invention generally contains a collection of ligands that have characteristics that are useful for determining the expression level of a molecule in a specimen. As used herein, the term "ligand" refers to a molecule that can selectively bind to a molecule in a specimen. The term selectively means that the binding interaction is detectable over non-specific interactions by a quantifiable assay. A ligand can be essentially any type of molecule such as a polypeptide, nucleic acid, carbohydrate, lipid, or any organic derived compound. Moreover, derivatives, analogues and mimetic compounds are also intended to be included within the definition of this term. Those skilled in the art know what is intended by the meaning of the term ligand. For example, the target can contain nucleic acids, which can be used to detect the presence and amount of nucleic acid or polypeptide molecules in a specimen. Similarly, the target can contain antibodies or binding molecules, which can be used to detect polypeptides or biochemical forms of polypeptides in a specimen. Generally, a target contains a sufficient number of ligands to generate an expression profile representative of the expression level of a sample of molecules in a population of molecules in a specimen from an individual. A variety of methods can be used to detect binding of specimen molecules to target ligands, as disclosed herein.

One skilled in the art can readily determine an appropriate number and type of ligands to include in a target for use in methods of the invention depending on the desired application. For example, a general target can be used to indicate the general health state of an individual for a variety of potential health states. Such a general target contains a relatively large number of ligands that provides a sufficient number of binding sites for a sample of molecules to indicate the health state of an individual. For example, a relatively large number of ligands can be about 500 or more ligands, about 1000 or more ligands, about 2000 or more ligands, about 3000 or more ligands, about 5000 or more ligands, or even about 10,000 or more ligands. A general target contains a variety of ligands, at least some of which can bind to a sample of molecules in a population of molecules in a specimen to be predictive of the health state of an individual.

A directed target can also be used when an expression profile of an individual is intended to indicate the health state of an individual with respect to a particular disease or group of diseases. With a directed target, the target can contain a smaller number of ligands since the ligands are directed to identifying sample molecules for a more limited number of health states, thereby requiring a smaller sample of molecules predictive of a particular disease or group of diseases. One skilled in the art can readily determine a sufficient number of ligands to include in a target to sample molecules in a population to indicate the health state of an individual, as described herein.

As used herein, the term "nucleic acid" or "nucleic acid molecule" means a polynucleotide such as deoxyribonucleic acid (DNA) or ribonucleic acid (RNA) and encompasses both single-stranded and double-stranded nucleic acid as well as an oligonucleotide. Nucleic acids useful in the invention include genomic DNA, cDNA, mRNA and synthetic oligonucleotides corresponding thereto and can represent the sense strand, the anti-sense strand, or both.

As used herein, the term "polypeptide" refers to a peptide or polypeptide of two or more amino acids. A polypeptide can also be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

A modification of a polypeptide, particularly ligand polypeptides, can also include non-naturally occurring derivatives, analogues and functional mimetics thereof generated by chemical synthesis, provided that such polypeptide modification displays a similar functional activity compared to the parent polypeptide. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

As used herein, a "summation value" refers to the sum of a given set of values. For example, a "positive summation value" refers to the sum of numbers assigned a positive value. Similarly, a "negative summation value" refers to the sum of numbers assigned a negative value.

The invention provides a method of determining a comparative expression profile in an individual. The method includes the steps of determining a multidimensional coordinate point representative of the expression levels of a sample of molecules in a population of molecules in a specimen from the individual; comparing the multidimensional coordinate point to a health-associated reference expression region of the sample of molecules; and determining if the multidimensional coordinate point is within or outside the health-associated reference expression region, wherein the multidimensional coordinate point within the health-associated reference expression region indicates a reference expression profile and wherein the multidimensional coordinate point outside the health-associated reference expression region indicates a perturbed expression profile.

The invention also provides a method of determining a comparative expression profile in an individual by comparing the expression levels of a sample of molecules in a population of molecules in a specimen from the individual with health-associated reference expression intervals of the molecules in the sample, wherein expression levels within the health-associated reference expression intervals indicate a reference expression profile and wherein expression levels outside the health-associated reference expression intervals indicate a perturbed expression profile. By comparing the expression levels of a sample of molecules to a health-associated reference expression interval, it can be determined whether the expression levels are within or outside the health-associated reference expression interval. The method of the invention can further comprise the step of inputting the expression level of the molecules in a specimen. Additionally, the method can further comprise the step of determining the expression levels of molecules in the specimen. For example, the expression level of a molecule can be determined by comparing the expression level of the molecule with a reference expression level correlated with a health-associated reference expression interval, for example, using direct quantitation methods such as ICAT. Also, the expression level of a molecule can be determined using binding methods by contacting a specimen with a target.

The invention additionally provides a method of determining a comparative expression profile in an individual by determining the expression levels of a sample of molecules in a population of molecules in a specimen from the individual; determining a multidimensional coordinate point representative of the expression levels of a sample of molecules; and comparing the multidimensional coordinate point with a health-associated reference expression region of the molecules in the sample, wherein the multidimensional coordinate point within the health-associated reference expression region indicates a reference expression profile and wherein the multidimensional coordinate point outside the health-associated reference expression region indicates a perturbed expression profile. The method can further include the step of determining an expression profile in an individual by contacting a specimen from the individual with a target.

The invention also provides a method of determining a comparative expression profile in an individual by determining the expression levels of a sample of molecules in a population of molecules in a specimen from the individual; and comparing the expression levels with health-associated reference expression intervals of the molecules in the sample, wherein expression levels within the health-associated reference expression intervals indicate a reference expression profile and wherein expression levels outside the health-associated reference expression intervals indicate a perturbed expression profile.

The invention further provides a method of determining a comparative expression profile in an individual by comparing the expression levels of a sample of molecules in a population of molecules in a specimen from the individual with reference expression levels correlated with health-associated reference expression intervals of the molecules in the sample, wherein expression levels within the health-associated reference expression intervals indicate a reference expression profile and wherein expression levels outside the health-associated reference expression intervals indicate a perturbed expression profile. Such methods of comparing the expression levels of a sample of molecules in a population with reference expression levels can similarly be applied to diagnose a disease or health state in an individual.

The invention additionally provides a method of determining an expression profile in an individual by contacting a specimen from the individual with a target; determining the expression levels of a sample of molecules in a population of molecules in the specimen; and comparing the expression levels with health-associated reference expression intervals of the molecules in the sample, wherein expression levels within the health-associated reference expression intervals indicate a reference expression profile and wherein expression levels outside the health-associated reference expression intervals indicate a perturbed expression profile.

In methods of the invention, a reference expression profile indicates a reference health state in the individual. A perturbed expression profile indicates a perturbed health state, that is, a health state that differs from the reference population, and can indicate a disease state in the individual or a predisposition to develop a disease when the reference population is healthy. The methods of the invention can therefore be used to diagnose a disease state or a predisposition to develop a disease, even though the individual has no signs or symptoms associated with the disease.

The methods of the invention for determining a comparative expression profile in an individual utilize a health-associated reference expression region based on a statistical sampling of the expression levels of molecules in reference individuals to determine the range of molecule expression levels. Determining a reference expression region for molecules provides a statistically determined expression profile of a reference population of individuals that allows comparison of the expression profile of an individual to determine if his or her expression profile falls within the range of expression levels of reference individuals or if the expression level of one or more molecules deviates from the reference range.

Once a health-associated reference expression interval has been determined for a given molecule, a specimen from any individual can be analyzed with respect to the expression level of that molecule. Similarly, once a health-associated reference expression region has been determined for a sample of molecules, a specimen from any individual can be analyzed with respect to the expression levels of the sample of molecules. A multidimensional coordinate point can be determined that is representative of the expression levels of the sample of molecules and compared to the health-associated reference expression region to determine if the expression level of that molecule lies within or outside the health-associated reference expression region and is therefore outside the perturbation limits of the health-associated reference expression region. Furthermore, the expression level can be compared with the health-associated reference expression interval to determine if the expression level of that molecule lies within the health-associated reference expression interval or lies above or below the perturbation limits of the health-associated reference expression interval.

The methods of the invention for determining a comparative expression profile in an individual can use multiple health-associated reference expression regions, where each region corresponds to a reference population of individuals. A multidimensional coordinate point for an individual that lies within one of these regions can be used to classify the individual as having the health state corresponding to the reference population of individuals represented by that region.

To obtain a statistical sampling of the expression levels of molecules in a reference individual, the expression levels of molecules in a population of reference individuals are determined by the methods disclosed herein. Once the expression levels of molecules in the population are determined, well known statistical analysis can be applied to provide a statistically useful reference expression region. If needed, the expression levels of additional reference individuals can be determined and added to the previously determined expression levels until statistically useful reference expression intervals are determined. Similarly, multiple reference expression regions can be determined from multiple reference populations.

Methods of the invention, for the purpose of determining the health state of an individual based upon expression profiles for the individual and for one or more reference populations, can include linear, non-linear, and/or multivariate calculations from fields including mathematics, statistics, and/or computer science. Such calculations can proceed in two phases: (1) an overall computation involving training and/or estimation using data from the reference population(s) and (2) a simpler computation for an individual using the results of phase 1. The end result of such calculations is to provide one or more qualitative or quantitative indicators of the health state of the individual.

A variety of calculations can be used in the methods of the invention. Exemplary calculations useful in methods of the invention include discriminant analysis, in which a new individual is classified from known calculations by training with a set of individuals of known classification. For example, data from individuals with known health states can be used to classify a new individual as having one of these known health states. Other exemplary methods include classification analysis, which is similar to discriminant analysis, and multiple discriminant analysis.

Cluster analysis is a collection of methods to find groups in a set of data. Cluster analysis can be used to find groups, for example, to group disease-associated molecules or to cluster individuals into groups of different health states. Such a method can be used to identify a sample of molecules from a larger population of molecules that are associated with a disease state or indicative of a particular disease or progression of a disease.

Analysis of variance (ANOVA) is a general statistical technique useful for testing the significance of differences between and among groups.

Regression analysis is a general statistical analysis for predicting based on observations and can be used, for example, to predict a health state. Logistic regression analysis can be used for the purpose of classification (see Example II). Regression trees is a predictive method based on a tree structure trained from a set of data. The data set can be based on the expression levels of molecules or combinations of molecules. Training is carried out with a series of decisions. For example, a first decision can be if a molecule or group of molecules is expressed at a high or low level. Then a decision can be based on the expression of another molecule or group of molecules, and so forth. The method is data-based and can be used for predicting the relationship between molecule expression levels and health state. Decision trees are similar to regression trees, but the emphasis is on making a decision, for example, deciding the health state of an individual. Nearest neighbor algorithms are distance based classification methods to assign the closest match to an individual and are useful for individual-to-individual comparison of complex components.

Principal components, factor analysis, multidimensional scaling and other methods of dimensionality reduction are methods to reduce the number of combinations of molecules for an effective classification. Likelihood models are methods using statistical data and probability models to provide optimal use of statistical information, where applicable. Likelihood models provide a specific description of the pattern of variation in data and can be used for estimation and hypothesis testing. Hypothesis testing is a formal process of using data to make decisions. Hypothesis testing can be used to test whether a molecule or set of molecules is useful and should be included in a group. Hypothesis testing can also be used to decide if a pool of individuals is significantly different from another pool or group of individuals.

Derived variables can be created and used to increase dimensionality beyond the number of molecules in order to help a statistical method achieve an effective classification. For example, interaction terms formed by multiplying the expression levels of selected pairs of molecules can be used.

Kernel density estimation and other smoothing techniques are methods used for the purpose of averaging out or eliminating noise in data or statistical variation in data. Cross-validation and other methods to guard against overfitting of the data are used in particular to protect against over optimism or over extension of data regarding the performance of a diagnostic system from a body of data. Cross-validation serves to prevent an overly optimistic appearance of the data, for example, a set of data can appear to be predictive of two distinct groups, where cross-validation can be used to compensate for an apparent overly optimistic appearance of the data. For example, if one observation is repeatedly omitted from a data set of individuals with known health states, its classification based on the remaining data can be used to obtain a more realistic indication of system performance.

The bootstrap and other statistical resampling techniques are methods used to resample from the data in order to assess the variability of the system computed from such data. Artificial intelligence, including artificial neural networks, machine learning, data mining, and boosting algorithms can also be used (see Example III). An artificial neural network is a computational method trained on a training set to make a new classification, for example, a training set of molecules in a reference population to classify a new individual. Machine learning is a collection of automated methods in which training can be used to learn what distinguishes a group, for example, groups of different health states, and is then used to classify an individual into a group. A boosting algorithm is an example of machine learning and is based on taking a simple system of classification methods to assemble more complex methods. For example, in a boosting algorithm, the expression levels of molecules taken one at a time can be analyzed in a particular sequence to generate a more effective method. Data mining is a method based on learning and inferring from large bodies of data and is useful for understanding how to use a large data set for calculations. Data mining is particularly useful when using large data sets, for example, examining a large number of sample molecules and/or a large reference population.

The methods of the invention can include a statistical calculation of the degree of confidence associated with the assignment of an individual to a health state. Accordingly, two individuals can both have multidimensional coordinate points within a particular health-associated reference expression region, for example, a region corresponding to reference individuals having cancer, but with different levels of confidence for the diagnosis, for example, one individual can have a 98% confidence of the diagnosis while the other individual has an 85% confidence.

Bayesian analysis using prior probability distributions is a method that uses expert opinion with prior probabilities along with observed data to make a decision. The method can therefore incorporate expert opinion to aid in decision making based on prior probability distributions.

Any one, or combination of two or more, of the statistical methods described above, or other statistical methods useful for characterizing the expression levels of molecules to determine the health state of an individual, can be used in methods of the invention.

Although the methods of the invention are based on determining the expression levels of molecules in a reference population, it is understood that the identity of the molecules need not be known. Thus, it is not necessary to know the identity of a particular specimen molecule that binds to a particular ligand, only that a specimen molecule that binds to a particular ligand has a measurable expression level that can be correlated with the health state of an individual. However, if desired, the identity of molecules having expression levels correlated with the health state of an individual can be determined, for example, using methods like ICAT, as described herein.

The methods of the invention can be applied to determining the expression profile corresponding to many physiological systems and states in the cell, for example, nervous, immune, cardiovascular, gastrointestinal, endocrine, hepatic, lymphatic, neuromuscular, renal, respiratory, skeletal, urogenital systems, and the like. Pathologies in these systems and perturbations in organs of these systems can be determined using methods of the invention. Furthermore, pathologies in various systems can be assessed using WBCs as a specimen from the individual, as described herein.

The methods of the invention are advantageous in that multiple parameters are analyzed to assess the health state of an individual. The methods of the invention can be used to analyze at least two and up to many molecules in a sample of molecules to determine the health state of an individual. Accordingly, a sample of molecules can contain 2 or more, 3 or more, 5 or more, 10 or more, 15 or more, 20 or more, 25 or more, 30 or more, 40 or more, 50 or more, 60 or more, 70 or more, 80 or more, 90 or more, 100 or more, 150 or more, or even 200 or more different molecules for which an expression level can be determined. Moreover, the sample molecules can contain 300, or more, 400 or more, 500 or more, 700 or more, or 1000 or more molecules. A sample can also contain 2000 or more, 3000 or more, 5000 or more, or even 10,000 or more molecules. When analyzing a sample containing a large number of molecules, the expression levels of the molecules can be conveniently performed using a target-based method such as an array. For example, in a specimen of 5000 molecules, if the expression level of 500 those molecules is correlated with the health of an individual, simultaneous measurement of the expression levels of those 500 molecules using methods of the invention provides information on the health of the individual.

The analysis of multiple parameters provides a convenient method to determine a comparative expression profile of an individual relative to one or more reference populations. The methods of the invention are useful for determining a comparative expression profile of an individual and providing a simplified output that allows a convenient analysis of the health state of an individual, for example, whether an individual is healthy, has a predisposition for a disease, or has a disease. Such methods can also be applied to determining the prognosis of a patient having a disease or to estimate the course of a disease.

The methods of the invention are advantageous in that the use of multiple parameters provides information on the expression levels of molecules that can be correlated with the health state of an individual by comparing the expression levels to one or more health-associated reference expression regions. The methods of the invention can be performed as a one-molecule-at-a-time analysis, where the expression level of individual molecules are compared to a health-associated reference expression region, including a health-associated reference expression interval. In a one-molecule-at-a-time multiparameter analysis, the analysis can be simplified, for example, by assigning a numerical value, which can be summed to generate a summation value that reflects the comparison of multiple parameters to a reference population, as described in more detail below. In a multidimensional multiparameter analysis, the analysis can be simplified by determining a multidimensional coordinate point that is compared to one or more health-associated reference expression regions defined by one or more reference populations, as described in more detail below. In both one-molecule-at-a-time and multidimensional analysis, the information obtained on multiple parameters, that is, the expression levels of multiple molecules, is preserved and is useful in determining the health state of an individual.

The methods of the invention are advantageous in that the expression level in an individual for any number of molecules can be characterized to determine an expression profile for the individual. The methods of the invention can be particularly advantageous when a large number of different molecules are being analyzed.

Although an individual having a disease or who is predisposed to developing a disease will have a change in expression of various molecules, not all molecules will necessarily have a change in expression. Furthermore, there can be a change in relative expression between two or more molecules, even though the expression levels of individual molecules are each within a health-associated reference expression interval. Therefore, whether a change in expression is observed depends on which particular molecule is characterized with respect to expression levels. For example, if the expression level of a particular molecule is determined, and if a change in expression level of that molecule or a change in relative expression to another molecule is associated with a disease or indicates a predisposition to developing a disease, then an expression profile based on determining the expression level of that molecule will reflect the health state of that individual. An individual having an expression level for that particular molecule within a health-associated reference expression interval is considered to have a reference health state, at least with respect to that particular molecule. In contrast, an individual having an expression level for that particular molecule outside a health-associated reference expression interval is considered to have a perturbed health state with respect to that molecule.

Although some diseases can be characterized, at least in part, by a change in expression of a particular molecule, generally a number of molecules exhibit changes in expression or change in relative expression in an individual having a disease state. Similarly, changes in expression of multiple molecules are also associated with a predisposition to developing a disease state, although the number of molecules having altered expression levels can be lower than in a disease state. Most diseases cannot be characterized by a change in a single molecule but are characterized by changes in expression of a variety of molecules, many of which can also have changes in expression in other diseases. For example, some of the molecules exhibiting changes in expression in an individual having a disease will be specific to the disease. However, other molecules exhibiting changes in expression will not be disease-specific but will be molecules exhibiting changes in expression in a variety of conditions. The methods of the invention are advantageous in allowing analysis of such diseases having complex changes in expression patterns by determining multiple parameters indicative of the health state of an individual.

Furthermore, even in diseases where mutations in a single gene contributes to a disease, these mutations are often associated with the activity or function of the gene or gene product but do not necessarily affect the expression level of the gene or gene product. For example, loss of p53 function is found in more than 50% of human tumors (Wang, *Anticancer Res.* 19:4759-4771 (1999); Hollstein et al., *Science* 253:49-53 (1991)). However, many of these loss of function mutations alter activity of p53 but not the level of p53 expression. Therefore, mutations in p53 that would be indicative of cancer could not be determined by the expression level of p53. Nevertheless, mutations in p53 which would lead to cancer would also lead to alterations in the expression levels of other molecules due to changes in the physiological state in response to the p53 mutations. Therefore, determination of the altered expression levels of these other molecules can be used to determine the health state of an individual, even in the absence of measurable changes in expression levels of disease-specific genes or gene products that cause or contribute to the disease such as p53 mutations that alter activity but not expression levels of p53.

The methods of the present invention are advantageous in that the methods allow multiparameter analysis of complex changes in expression patterns associated with a disease or predisposition for a developing a disease, which can be converted to a simplified output that allows determination of the health state of an individual. In particular, the methods of the invention are applicable to determining whether an individual has substantially the same health state as a reference population or a perturbed health state, including a disease state or predisposition to developing a disease. Thus, a series of parameters, based on the expression level of a sample of molecules in a population of molecules in a specimen, for example, mRNA, proteins or small molecules from leukocytes, or proteins or small molecules from serum, can be measured to determine the health state of an individual.

A comparative expression profile of an individual can be determined based on comparing the expression level of a molecule in a specimen from the individual with a health-associated reference expression interval of the molecule. Similarly, a comparative expression profile of an individual can be determined based on comparing the relative expression levels of two or more molecules in a sample, for example, by determining a multidimensional coordinate point representative of the expression levels of the molecules, to one or more health-associated reference expression regions corresponding to the molecules. Although a multidimensional coordinate point can be determined for a multidimensional analysis, it is understood that the expression levels of individual molecules can be compared to the health-associated reference expression region so long as the region reflects the relative expression of the sample of molecules in the reference population.

The methods of the invention can be used to characterize a health state based on any number of sample molecules, including large numbers of sample molecules. The analysis of large numbers of molecules can be particularly useful when trying to discriminate between diseases having similar but distinct changes in expression patterns. If desired, an expression profile based on the determination of the expression levels of essentially all molecules expressed in a specimen can be determined so long as the health-associated reference expression region of a sample of molecules in a population of molecules in the specimen is statistically useful for predicting the health state of an individual.

For example, in a one-molecule-at-a-time analysis, a numerical value can be assigned indicating whether the expression level of a particular molecule in a specimen falls within a health-associated reference expression interval corresponding to a statistical sampling of a reference population. Assigning a numerical value based on whether an expression level falls within a health-associated reference expression interval or lies outside the perturbation limits of such a reference expression interval allows a potentially complex analysis of the expression profile of many molecules to be conveniently converted to a simplified numerical output that provides insight into the health state of an individual.

The invention provides additional methods of determining a comparative expression profile in an individual. One such method includes the steps of (a) comparing the expression level of a molecule in a specimen from an individual with a health-associated reference expression interval of the molecule; and (b) assigning a value of 0 if the expression level is within the health-associated reference expression interval or assigning a positive numerical value if the expression level is outside the health-associated reference expression interval, wherein an expression level within the health-associated reference expression interval indicates a reference expression profile and wherein an expression level outside the health-associated reference expression interval indicates a perturbed expression profile. The method can further include repeating steps (a) and (b) one or more times.

Accordingly, methods of the invention can include the step of assigning a numerical value depending on whether the expression level of a molecule is within a health-associated reference expression interval for that molecule or whether the expression level of the molecule is outside the health-associated reference expression interval. For example, if the expression level of a molecule is within a health-associated reference expression interval, a value of 0 is assigned to the expression level of the molecule in a particular specimen. In such a case, a value of 0 indicates that the individual has a reference expression profile, at least with respect to the particular molecule for which an expression level was determined. Such an analysis can similarly be applied to the determination of the expression level of two or more molecules or any number of molecules. In the case where the expression level of each of the sample of molecules analyzed lies within its corresponding health-associated reference expression interval, a value of 0 is assigned to the expression level of each molecule. Accordingly, if 0 is assigned to the expression level of each sample molecule analyzed, the individual has a reference expression profile. An individual having a reference expression profile can have a reference health state, that is, a health state that is substantially the same or similar to a reference population of individuals.

If the expression level of a molecule is outside a health-associated reference expression interval for that molecule, a positive numerical value can be assigned to the expression level of the molecule in a particular specimen. For example, in a simplified case, the positive numerical value can be 1. In such a case, a value of 1 indicates that the individual has a perturbed expression profile. Such an analysis can similarly be applied to the determination of the expression level of two or more molecules or any number of molecules. For each molecule having an expression level outside its health-associated reference expression interval, a positive numerical value is assigned. In such a case, each molecule having an expression level that is below or above the perturbation limits of a health-associated reference expression interval for that molecule is assigned a positive numerical value, indicating a deviation from a reference expression range. Accordingly, if a positive numerical value is assigned to the expression level of one or more molecules analyzed in a sample of molecules, the individual has a perturbed expression profile. An individual having a perturbed expression profile indicates that the individual has a perturbed health state, and such an individual can have a disease state, a predisposition to developing a disease, a prognosis associated with a disease or treatment of a disease, and such an indicated perturbed health state can also be used to estimate the course of a disease.

When the expression level of a relatively small number of molecules is determined and compared to corresponding health-associated reference expression intervals for each respective molecule, the determination of whether the expression level of molecules indicates a reference expression profile or a perturbed expression profile is straightforward. However, as the number of molecules analyzed increases, the analysis becomes more difficult. The methods of the invention in which numerical values are assigned to the expression level of a molecule based on whether the expression level is within or outside a health-associated reference expression interval provide a simplified output that can be particularly useful when a large number of molecules are analyzed.

One approach to simplifying the analysis of an expression profile based on a larger number of molecules is to sum the values assigned to the expression levels of the molecules to generate a summation value. For example, if 100 molecules are analyzed and none deviate from their respective health-associated reference expression intervals, the summation value would be 0, indicative of a reference expression profile. On the other hand, if at least one of the molecules analyzed has a value of at least 1, the summation value would be at least 1. Thus, a summation value of 1 or greater indicates a perturbed expression profile. As the number of molecules having expression levels outside their respective health-associated reference expression intervals increases, the summation value correspondingly increases. Thus, higher summation values indicate a larger number of molecules having expression levels outside reference ranges.

For example, in the simplified exemplary case where the expression level of 100 molecules is characterized and a positive value of 1 is assigned to those deviating from their respective health-associated reference expression intervals, a summation value of 5 indicates that 5 molecules have expression levels either higher or lower than the range for reference individuals. Such a summation value of 5 can be indicative of a disease state or a predisposition to developing a disease. Similarly, a summation value of 10 indicates that 10 molecules have expression levels either higher or lower than the range of reference individuals. Thus, the summation value provides a simplified analysis characteristic of the expression profile of the individual.

Moreover, the higher the summation value, the greater the number of molecules having expression levels outside the reference range and the more likely that such an individual has a disease. For example, it is possible that an individual having expression levels of 5 molecules outside the reference range indicates that the individual is predisposed to developing a disease. However, it is possible that a person having 10 molecules outside the reference range indicates that the individual has a disease. Thus, the methods of the invention can be used to determine the health state of an individual, including determining whether an individual has a disease state or a predisposition to developing a disease. The methods of the invention are thus applicable to determining the likelihood of an individual having a predisposition to developing a disease or the likelihood that an individual has a disease.

The methods of the invention can include the step of assigning positive numerical values, and, in such a case, the value assigned to any individual molecule can be weighted depending on the likelihood that expression of the molecule outside the health-associated reference expression interval is correlated with a disease or predisposition to developing a disease. For example, as described above, decrease or loss of p53 activity, including loss of p53 expression, is found in a variety of cancers (Hollstein et al. supra, 1991). Thus, a decrease or loss of p53 expression has a high degree of correlation with the development of cancer. Accordingly, a decrease in expression of p53 to a level below the health-associated reference expression interval can be assigned a higher numerical value, or a weighted value, since its expression is correlated with a predisposition to developing cancer or with having cancer. In contrast, a molecule that has an increase in expression that is correlated with cancer and with benign conditions can be given a lower numerical value.

A method of the invention in which a summation value is generated based on the assignment of weighted numerical values can provide greater sensitivity in discriminating between conditions. For example, assume that a change in expression of 10 molecules is associated with a benign condition and a malignant condition. However, the 10 molecules having aberrant expression in the benign condition are not identical to the 10 molecules having aberrant expression in the malignant condition. As an example, assume that aberrant expression of 5 molecules is common to both the benign and malignant conditions. Such molecules can be assigned a relatively low numerical value. The 5 molecules associated with the benign condition can be given an intermediate value, whereas the 5 molecules associated with the malignant condition can be given a relatively high value. In such a case, an individual having the benign condition can be readily distinguished from an individual having the malignant condition based on the summation value since an individual with the benign condition would have a lower summation value than an individual having the malignant condition.

In addition to assigning weighted values based on which particular molecules have expression levels outside a health-associated reference expression interval, weighted values can also be assigned based on the relative amount of expression. Assigning weighted values based on relative deviation from health-associated reference expression intervals is particularly useful when the expression of a molecule varies with the severity of a disease. For example, a level of expression that is just outside the perturbation limits of a health-associated reference expression interval can be assigned a lower value, and a higher value can be assigned the further the expression level deviates from the perturbation limits.

Weighting can also be used when there is some knowledge that expression levels of a particular molecule is correlated with a condition. For example, variable expression levels of insulin receptor appear to be correlated with the severity of associated disease (Taylor, *Diabetes* 41:1473-1490 (1992)). Patients with leprachaunism have mutations in both insulin receptor gene alleles and have an extreme degree of insulin resistance. In contrast, many patients with type A insulin resistance have mutations in only one allele of the insulin receptor gene. Moreover, patients with type A insulin resistance having mutations in both alleles of the insulin receptor gene tend to have fasting hyperglycemia and overt diabetes mellitus in contrast to patients with single mutant alleles, who tend to have glucose intolerance despite normal levels of fasting glucose. In such a case, assignment of a weighted value based on the relative decrease in expression level of insulin receptor can be used to distinguish various levels of insulin resistance or a predisposition to developing insulin resistance.

Similarly, overexpression of HER2/neu is associated with poor patient outcome in breast cancer patients (Slamon et al., *Science* 235:177-182 (1987); Slamon et al., *Science* 244:707-712 (1989)). Assigning a weighted value based on the relative increase of HER2/neu expression above the perturbation limit of a health-associated reference expression interval of HER2/neu can be used as a prognostic indicator of the likely progression of the disease. An indication of an expression level of a molecule that is associated with the progression of a disease can further be optionally combined with additional prognostic markers having altered expression, to adjust the aggressiveness of therapy or determine a particular type of therapy.

Another useful application of weighting is based on a threshold of change in expression. For example, it is possible that an increase in expression of a molecule above the health-associated reference expression interval is correlated with a predisposition to developing a disease whereas an increase in expression of a particular magnitude is correlated with having the disease. In such a case, a lower weighted value can be assigned if the expression level of the molecule exceeds the perturbation limit of the health-associated reference expression interval and a higher weighted value can be assigned if the expression exceeds the threshold limit associated with the disease. Depending on the desired diagnostic application, one skilled can determine a desirable level of weighting. Thus, the assignment of weighted values can be used to further distinguish the expression profile of individuals to determine the health state of an individual.

The invention additionally provides a method of determining a comparative expression profile in an individual by (a) comparing the expression level of a molecule in a specimen from the individual with a health-associated reference expression interval of the molecule; and (b) assigning a value of 0 if the expression level is within the health-associated reference expression interval, assigning a positive numerical value if the expression level is greater than the health-associated reference expression interval, or assigning a negative numerical value if the expression level is less than the health-associated reference expression interval, wherein an expression level within the health-associated reference expression interval indicates a reference expression profile and wherein an expression level outside the health-associated reference expression interval indicates a perturbed expression profile. A method of the invention can further include repeating steps (a) and (b) one or more times.

Methods of the invention described above include the step of assigning a positive numerical value if the expression level of a molecule is outside a health-associated reference expression interval. Although such methods are useful for determining an expression profile of an individual, such methods nevertheless provide a simplified output of information. For example, it is possible that a molecule is overexpressed in certain conditions and underexpressed in other conditions. Using methods of the invention in which a positive numerical value is assigned when the expression level of a molecule is either above or below the perturbation limits of the health-associated reference expression interval can mask the distinction between a disease in which the molecule is increased and a disease in which the molecule is decreased. In contrast, a more detailed expression profile can be obtained using a method that utilizes this expression information.

One approach to obtaining a more detailed expression profile is to use methods in which information on the relative change in expression levels is incorporated. The invention thus provides methods in which an expression level exceeding the upper perturbation limit is assigned a positive numerical value and an expression level less than the lower perturbation limit is assigned a negative numerical value. As such, information on the relative increase or decrease in expression of a molecule is preserved.

For example, if a molecule has increased expression in one disease and decreased expression in another disease, these changes can be assigned corresponding positive and negative numerical values that reflect an increase or decrease, respectively, in expression outside a health-associated reference expression interval. In contrast to the methods in which both the increase and decrease are assigned positive numerical values, the assignment of positive and negative values that correspond to an increase or decrease in expression outside a health-associated reference expression interval preserves additional information that is reflected in the expression profile of an individual. In the above example, such information can be used to distinguish between the disease in which a molecule has increased expression above an upper perturbation limit of a health-associated reference expression interval and the disease in which a molecule has decreased expression below the lower perturbation limit. As with other methods of the invention, the numerical value assigned can be weighted depending on the desired application of the methods.

As described above, positive numerical values can be assigned to expression levels outside a health-associated reference expression interval regardless of whether the expression level of a molecule is above or below the perturbation limit. However, a similar analysis can be accomplished when positive and negative values are assigned by simply using the absolute values of the negative numbers. Thus, the methods of the invention can include summing the absolute values of positive and negative values to generate a summation value. In such a case, a summation value of 1 or greater indicates an individual has a perturbed expression profile. Similarly, methods of the invention can include the use of mathematical functions other than the absolute value function.

For simplicity, the methods described above assign positive and negative values to reflect an expression level above or below, respectively, the perturbation limits of a health-associated reference expression interval. However, it is understood that the methods can use any type of identifier that is useful for determining an expression profile, including positive and negative numbers for expression levels below and above a perturbation limit or letter identifiers. Furthermore, identifiers can be included to reflect categories of molecules that are associated with specific diseases such as diabetes or cancer. One skilled in the art can readily determine the appropriate type of values to assign, for example, appropriate weighted numerical values or inclusion of identifiers, depending on the particular application of the methods of the invention. As with one-molecule-at-a-time analysis described above, weighting can also be used in multidimensional analysis.

The above-described one-molecule-at-a-time analysis of multiple parameters is directed to preserving information about an individual's health state based on the determination of expression levels of a sample of molecules from a specimen of the individual. In addition, the expression levels of reference molecules can also be analyzed in a multidimensional analysis using statistical methods, as disclosed herein (also see Examples I, II and III). Instead of comparing the expression levels of individual molecules of a sample to the corresponding health-associated reference expression intervals determined for a reference population, as in one-molecule-at-a-time analysis, the expression level of each molecule in the sample is compared to other molecules in the sample in a multidimensional analysis. The expression of the sample of molecules in an individual is then compared to one or more health-associated reference expression regions of the same sample of molecules from one or more populations of reference individuals. Therefore, a multidimensional analysis can examine the relative expression of a sample of molecules, allowing more subtle changes in expression patterns to be correlated with the health state of an individual than provided by a one-molecule-at-a-time analysis.

A simplified example of a multidimensional analysis is shown in FIG. 1. FIG. 1 shows a schematic diagram of a hypothetical health-associated reference expression region. The circles represent multidimensional coordinate points representative of the expression levels (in arbitrary units) of two molecules in an individual. Therefore, each circle represents a coordinate point in multidimensional space, in this example two-dimensional space, that is defined by the expression levels of two molecules in an individual. The elliptical shaped region shows the clustering of expression levels of a reference population into a classification region, which is determined by applying statistical methods as disclosed herein. In this example, a region in two-dimensional shape space is classified as a health-associated reference expression region.

In the top panel of FIG. 1, one coordinate lies outside the health-associated reference expression region. The individual corresponding to this coordinate has expression levels of molecules 1 and 2 outside the health-associated reference expression intervals for those molecules, that is, molecule 1 is expressed at a higher level than in the reference population and molecule 2 is expressed at a lower level than the reference population. The determination of the perturbation limits of the health-associated reference expression region and whether an individual's coordinate lies within the region can be determined using statistical analysis, as disclosed herein.

Multidimensional analysis can provide additional insights into the expression profile of an individual than would be apparent from a one-molecule-at-a-time analysis of individual molecules. The bottom panel of FIG. 1 shows an individual having a coordinate that lies outside the health-associated reference expression region. In this case, the expression levels of both molecules 1 and 2 are within health-associated reference expression intervals for the respective molecules, that is, molecules 1 and 2 are expressed within the same range as the reference population. Nevertheless, by comparing the two molecules relative to each other, a deviation from the health-associated reference expression region can be observed. Thus, a multidimensional multiparameter analysis can reveal more subtle changes in an expression profile that can be useful in determining the health state of an individual.

Figure 2:
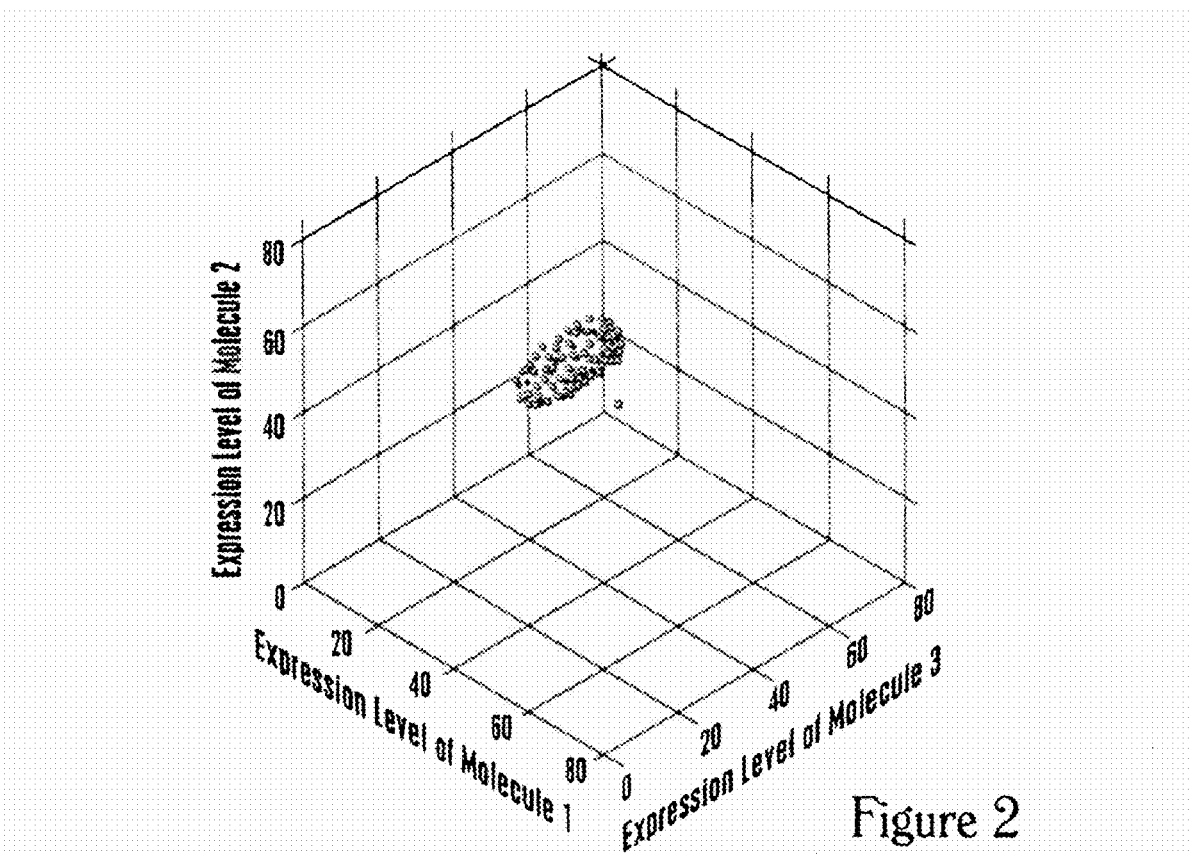
FIG. 2 shows a schematic diagram of a hypothetical health-associated reference expression region. The circles represent multidimensional coordinate points representative of the expression levels (in arbitrary units) of three molecules in an individual. Shown is a health-associated reference expression region of reference individuals in three-dimensional space as a region of coordinate points and the coordinate point of an individual that lies outside the health-associated reference expression region.

A multidimensional analysis can be performed with additional parameters. For example, a multidimensional analysis can be performed in three dimensional space (see FIG. 2). FIG. 2 shows a schematic diagram of a hypothetical health-associated reference expression region in three-dimensional space. In this case, each coordinate point represents the expression levels of three molecules in an individual, which define a three-dimensional coordinate point. A three-dimensional ellipsoid represents a health-associated reference expression region in three-dimensional shape space. Also shown is an individual having coordinate points that lie outside the health-associated reference expression region. As described above for two-dimensional analysis, statistical methods are applied to determine the perturbation limits of the three-dimensional health-associated reference expression region and to determine whether an individual has expression levels of molecules or a representative multidimensional coordinate point within the region.

In addition to two- and three-dimensional analysis, a similar analysis can be applied in n-dimensional space, where n is the number of molecules in a sample of molecules, that is, the number of molecules sufficient to predict the health state of an individual. In such a case, a health-associated reference expression region is defined in n-dimensional shape space based on the n-dimensional coordinate points of a reference population of individuals. Again, statistical methods are applied in multidimensional analysis to determine the perturbation limits of the n-dimensional health-associated reference expression region and to determine whether an n-dimensional coordinate point of an individual is within or outside the region.

The methods of the invention using multiparameter analysis are particularly useful for analyzing larger numbers of molecules in a sample and can provide insights into the expression profile of an individual that are not revealed when using a one-molecule-at-a-time analysis. Another advantage of multidimensional analysis is that the expression levels of molecules need not be compared to the same type of molecule but, instead, can be compared to any type of molecule that is expressed in an individual and can be correlated with the health state of an individual. Therefore, the expression levels of nucleic acids can be compared to the expression levels of polypeptides in a multidimensional analysis, with each molecule compared to other molecules in the sample. Similarly, nucleic acids or proteins can be compared to small molecules, or nucleic acids, proteins and small molecules can be compared relative to each other. Essentially any type of specimen molecules can be used, alone or in combination with other types of molecules, as a sample of molecules to determine the health state of an individual. Since there can be a discordance between mRNA expression and expression of the corresponding encoded protein, such a comparison between different types of specimen molecules can be useful for monitoring changes associated with the health state of an individual.

In an individual having a predisposition to developing a disease, or who is in early stages of a disease, the individual often will exhibit no signs or symptoms associated with the disease. For example, in early stages of cancer, an individual can feel healthy. Early detection of diseases such as cancer or determining an individual's susceptibility to a disease can be useful for treating an individual prophylactically, before signs or symptoms of the disease develop. An individual having a predisposition to developing a disease or who is in early stages of a disease can exhibit more subtle changes in expression than an individual exhibiting more overt symptoms of a disease. Multidimensional multiparameter analysis can be particularly useful in identifying more subtle changes in expression of molecules associated with early stages of disease and can therefore be used advantageously in preventative medicine.

The methods of the invention are advantageous in that an expression profile can be analyzed to determine the health state of an individual. Such methods are useful for routine health screening to determine if an individual has a reference health state, particularly if the reference individuals are healthy, or perturbed health state that requires further medical analysis or monitoring or that indicates a particular disease or a predisposition to develop a particular disease. Thus, the methods of the invention are useful in a variety of applications for predictive medicine and preventive medicine.

The methods of the invention are based on obtaining a health-associated reference expression region of a group of any number of molecules that are useful in diagnostic applications for determining the health state of an individual. A health-associated reference expression region is determined by obtaining information on the expression levels of a group of molecules in a population of reference individuals. One skilled in the art can readily determine the number of individuals to be included in a population to obtain a statistically useful health-associated reference expression region, as disclosed herein (see, for example, Anderson, *An Introduction to Multivariate Statistical Analysis*, second ed., section 6.7, Wiley, N.Y. (1984); Tietz *Textbook of Clinical Chemistry*, 3rd ed., Burtis and Ashwood, eds., W.B. Saunders Co., Philadelphia, Chapters 11-14, pp. 265-355 (1999)). For example, once the expression levels of a sample of molecules have been determined based on a given sized population, one skilled in the art can determine if the population size is sufficient for use in methods of the invention by applying any of a number of statistical methods to the determined health-associated reference expression region and assessing the usefulness of the health-associated reference expression region for predicting the health state of an individual (see Example I). Using such statistical methods allows a prediction of the statistical usefulness of a health-associated reference expression region for use in methods of the invention.

The number of individuals to include in a population for determining a health-associated reference expression region can vary depending on the particular application. For example, if a particular molecule is found to have a narrow range of expression variability in a reference population, a health-associated reference expression region for that molecule or for that molecule relative to another sample molecule can be obtained with a smaller population. In contrast, if a particular molecule is found to have a wide range of expression variability in a reference population, a larger population can be used for the statistical analysis to determine a health-associated reference expression region.

In a method of the invention in which the expression levels of two or more molecules are determined and compared to a health-associated reference expression region, each health-associated reference expression interval for each molecule need not be determined with an identical population. The health-associated reference expression interval for each molecule is based on a number of individuals in a population sufficient to make a statistically useful determination of the health-associated reference expression interval, although larger populations can be included.

A reference population can be selected on a variety of criteria based on the particular application of methods of the invention. Exemplary criteria for selection of reference individuals include the health state such as healthy individuals or individuals having a particular disease, age, gender, ethnic background, drug use, alcohol consumption or other criteria. Thus, if desired, a reference population can be focused on particular criteria. Alternatively, the reference population can contain a variety of individuals having various physiological states, but the reference population is partitioned into subgroups (see Solberg, *Tietz Textbook of Clinical Chemistry*, 3rd ed., Burtis and Ashwood, eds., W.B. Saunders, Philadelphia, Chapter 14, pp. 336-355 (1999)).

One skilled in the art can readily determine an appropriate reference population based on the particular application of methods of the invention. The methods of the invention use health-associated reference expression regions for comparison to the expression levels of a sample of molecules in a specimen from an individual to determine his or her health state. The size of the reference population depends on the criteria used to select reference individuals. Depending on the selection criteria and particular application of the methods of the invention, the reference population can be a relatively small number to a large number of individuals, including thousands of individuals.

The size of the reference population that is sufficient to determine a health-associated reference expression region for a group of molecules depends on the variability in expression of the molecules in the reference population and also on the degree of statistical separation from other reference populations. In some cases, the variability in expression of the molecule in a population is due to genetic variation in the population. The greater the genetic variation, the larger the reference population is needed to provide a statistically useful health-associated reference expression region. Accordingly, a smaller population can be used if reference individuals have a similar genetic background. For example, the closest genetic relationship to an individual is exhibited by an identical twin. It is therefore possible to compare the expression levels of molecules in an individual to the expression levels of the molecules in an identical twin of the individual having appropriate reference criteria, for example, an identical twin that is healthy. In such a case, an individual's expression profile can be compared to health-associated reference expression levels of molecules found in the identical twin to determine the health state of the individual.

Beyond an identical twin, the individuals having the next closest genetic similarity are family members who are blood relatives of an individual for which determination of a comparative expression profile is desired. Thus, family members having appropriate reference criteria can be used as a reference population. Due to the genetic similarity of family members, a relatively small population can be used to determine useful health-associated reference expression intervals, for example, populations of about 2 or more, about 3 or more, about 5 or more, about 10 or more, about 20 or more, about 30 or more, about 50 or more, or about 100 or more individuals. As described above, a reference population of family members is particularly useful for identifying molecules having such variability in expression that they are disregarded as molecules having expression levels correlated with the health state of an individual.

A reference population of family members can also be useful for determining polymorphic variations. For example, two unrelated families can be used as separate reference populations to determine expression levels of molecules. If desired, the family members can be selected so that the family reference population is representative of a healthy population. A similar analysis can be performed on a genetically unrelated family. Thus, the expression levels of molecules in two reference, healthy populations are determined. As described above, such a population of related family members will exhibit less genetic variability than a population of unrelated individuals. By comparing two genetically unrelated but healthy reference populations to each other, molecules exhibiting variable expression between the two reference populations most likely represent genetic variability rather than a disease-specific variability. Such a comparison can be useful for identifying those molecules exhibiting variability that is not associated with a disease state, and such molecules can accordingly be disregarded as molecules having expression levels correlated with the health state of an individual. Such a comparison, in combination with a comparison of reference health state and a disease state, can thus be used to identify sample molecules that are correlated with the health state of an individual.

Still another group of individuals having genetic similarity are individuals in a particular ethnic group. Thus, a reference population can be selected from individuals in an ethnic group to determine health-associated reference expression intervals. Such a reference population would include a larger population than a reference population of family members since the genetic variation in an ethnic group would be greater than in family members, for example, about 5 or more, about 10 or more, about 20 or more, about 30 or more, about 50 or more, about 100 or more, about 200 or more, about 500 or more, about 1000 or more, about 2000 or more, about 5000 or more, or even greater numbers of individuals. The expression levels of molecules in an individual of a particular ethnic background can be compared to a health-associated reference expression region determined for the ethnically related reference population. Using a health-associated reference expression region from a particular ethnic group can be desirable if the perturbation limit for one or more molecules expressed in that ethnic group lies within the health-associated reference expression intervals of those molecules for the general population and if aberrant expression of that molecule is associated with a disease in that ethnic group.

Still larger populations of reference individuals are used when the reference individuals are selected from the general population and are not directed to a specific ethnic group. In such a case, the reference individuals can represent a relatively random sampling of a general population, which can include a sufficient number of individuals from a sufficient variety of ethnic groups to be representative of the general population, for example, about 10 or more, about 20 or more, about 30 or more, about 50 or more, about 100 or more, about 200 or more, about 500 or more, about 1000 or more, about 2000 or more, about 5000 or more, about 10,000 or more, or even greater numbers of individuals. Selection of a sufficient variety of ethnic groups allows the genetic variance between ethnic groups to be incorporated into the health-associated reference expression region. Since a general population will have greater genetic variation, a larger population of reference individuals is used to determine a health-associated reference expression region. The number and variety of ethnic groups to include in a general reference population can be determined by one skilled in the art depending on the ethnic diversity of test individuals for which a comparative expression profile is to be determined.

The use of a reference individual or reference population can also be applied to identify a sample of molecules in a population of molecules useful for determining the health state of an individual. For example, if an expression profile of an individual having a disease is determined and compared to a related family member or family members, the molecules having differences in expression can include a sample of molecules indicative of the health state of an individual. The expression levels of those molecules exhibiting differences in expression can be determined in a reference population. For example, those molecules having statistically useful health-associated reference expression intervals represent a sample of molecules in a population of molecules. Accordingly, the sample of molecules can vary depending on the particular disease, and disease-specific samples can be determined by characterizing the expression profile in individuals having a variety of diseases, if desired. For example, disease-specific samples of molecules can be detected on directed targets containing corresponding ligands that bind to the sample of molecules.

Another method of identifying a sample of molecules useful for predicting the health state of an individual is to pool groups of reference individuals for comparison. Rather than individually measuring the expression levels of molecules in each individual of a reference population, specimens from reference individuals can be pooled. For example, healthy reference individuals can be pooled to generate a healthy reference pool, and individuals having a particular disease can be pooled separately from the healthy reference pool. The pooled reference populations can then be used to determine the expression levels of molecules in specimens from the pooled populations. The determined expression levels of such a pooled population is essentially an average of the population. The "average" expression levels determined for the separate reference populations can be compared, and such a comparison is expected to reveal molecules having differential expression between the pooled samples. Such a set of differentially expressed molecules can be used as a sample of molecules predictive of the health state of an individual having the disease of the pooled disease reference population. Identification of disease-specific molecules can be useful for identifying target ligands for a directed target. Such an analysis can be used for a dimensionality reduction, in which a smaller set of molecules is used as a predictor of the health state of an individual. Dimensionality reduction can therefore be useful in identifying a sample of molecules predictive of the health state of an individual.

Using a pool of reference individuals to identify a sample of molecules predictive of the health state of an individual is useful for simplifying the initial analysis and identification of a sample of molecules because it can provide a qualitative and quantitative analysis of the differential expression between two populations having different health states without the need to perform assays on many individuals separately. Essentially one assay can be performed for each pool of reference populations rather than individual assays on each member of the population. Accordingly, if desired, large numbers of individuals can be pooled, including hundreds, thousands, or tens of thousands of individuals, including, about 10,000, about 20,000, about 30,000, about 40,000 or even about 50,000 or more individuals, and conveniently assayed as essentially one specimen.

In addition to pooling a reference population corresponding to a particular disease, a pooled population can also be of individuals diagnosed with a variety of diseases. Rather than identifying a sample of molecules useful for diagnosing a particular disease, a pooled population having a variety of diseases can be useful in a more general diagnostic assay for determining the health state of an individual since a sample of molecules identified by such a pool would contain molecules that varied in expression in a variety of disease states.

Similarly, a pool of reference individuals having physiological perturbations can be pooled. Such physiological perturbations can include, for example, fasting, drug intake or drug withdrawal, exercise, and the like, as disclosed herein. Furthermore, a population of individuals having physiological perturbations can be pooled with disease individuals to identify a more general set of sample molecules useful for determining a variety of health states. Such methods of pooling disease and physiologically perturbed populations can be useful for identifying a sample of molecules and appropriate ligands for identifying those molecules on a general target. The sample molecules identified by such pooled populations of disease and physiologically perturbed individuals can also include molecules whose relative expression changes, even though individual molecules are expressed within a healthy reference population, as disclosed herein (see FIG. 1).

Exemplary physiological perturbations include fasting, drug intake or withdrawal, exercise, and the like. For example, physiological perturbations can include fasting, which is often used for lipid measurements or other physiological changes that are more immediately affected by diet. Physiological perturbations can include a resting state or sleep state, or can include exercise, for example, a stress test or other form of physical exertion. A physiological perturbation can also include the administration of safe compounds or drugs to test physiological responses of an individual. For example, glucose tolerance can be used to measure insulin response. Nitroglycerin can be administered for vasodilation and to determine patient habituation. Any of a variety of drugs or compounds that alter physiology but are known to be safe and well tolerated by most individuals can be used to physiologically perturb an individual and measure associated changes in expression of molecules.

The methods of the invention can thus be used to diagnose disease states or perturbed physiological states. The methods of the invention can also be used to identify changes in expression in response to drug treatment. Thus, by monitoring various populations of individuals, the methods of the invention can be used to predict the efficacy of a particular drug treatment based on changes in expression of specimen molecules. Multidimensional multiparameter analysis is particularly useful for analyzing more subtle changes in expression of molecules that can be associated with the treatment of a disease.

A population of individuals sufficient to obtain a health-associated reference expression interval for a general population of individuals would generally contain, tens, hundreds or thousands of reference individuals, depending on the method of determining expression levels as well as the variability in expression of the sample of molecules representative of the health state of the reference population. For example, the population can contain, for example, about 20 or more, about 30 or more, about 50 or more, about 100 or more, about 200 or more, about 500 or more or about 1000 or more individuals. A population can also contain about 2000 or more, about 3000 or more, about 4000 or more, or even about 5000 or more individuals. Additionally, a population can contain about 7000 or more, about 10,000 or more, about 15,000 or more or even about 20,000 or more individuals, depending on the particular application. One skilled in the art can readily determine an appropriate sized population to determine a health-associated reference expression interval based on statistical analysis of the determined reference expression ranges (see, for example, Solberg, supra, 1999).

Once a health-associated reference expression interval has been obtained for a sufficient number of molecules for a particular application, a comparative expression profile can be determined. A comparative expression profile is determined by comparing the expression levels of a sample of molecules in a population of molecules to a health-associated reference expression interval for each molecule. Such a comparative expression profile can be conveniently converted to a useful output, for example, by assigning values as described above in a one-molecule-at-a-time analysis or by comparing the expression levels of the sample of molecules to one or more health-associated reference expression regions in a multidimensional analysis.

To determine the expression level of a molecule in an individual, a specimen is obtained from the individual that is representative of the expression level of molecules in the individual. A specimen can be obtained from an individual as a fluid or tissue specimen. For example, a tissue specimen can be obtained as a biopsy such as a skin biopsy, tissue biopsy or tumor biopsy. A fluid specimen can be blood, urine, saliva or other bodily fluids. A fluid specimen is particularly useful in methods of the invention since fluid specimens are readily obtained from an individual. Methods for collection of specimens are well known to those skilled in the art (see, for example, Young and Bermes, in *Tietz Textbook of Clinical Chemistry*, 3rd ed., Burtis and Ashwood, eds., W.B. Saunders, Philadelphia, Chapter 2, pp. 42-72 (1999)). A specimen can optionally be fractionated into cell populations or subpopulations. A particularly useful method of fractionating a population of cells is to use ligands that bind to a cell surface molecule, for example, antibodies that bind to a cell surface antigen.

If desired, multiple specimens from an individual can be combined and analyzed as a single specimen representative of the expression levels of molecules in an individual. Alternatively, multiple specimens from an individual can be separately used to determine expression levels of molecules in the different specimens, and then the expression levels from multiple specimens compared or averaged, so long as the specimens from the reference population are treated in the same manner or the expression levels are correlated with appropriate controls and/or validation methods, as disclosed herein.

A specimen useful in methods of the invention contains one or more molecules that are representative of the gene expression level and/or cellular expression level of molecules in the individual. Methods for obtaining specimens that preserve the expression profile of molecules in a specimen, including nucleic acids such as mRNA, polypeptides, small molecules, or post-translational modifications of such molecules, are well known to those skilled in the art. Such methods include the use of appropriate buffers and/or inhibitors, including nuclease, protease and phosphatase inhibitors, that preserve or minimize changes in the expression level of molecules in the specimen. Such inhibitors include, for example, chelators such as ethylenediamne tetraacetic acid (EDTA), ethylene glycol bis(P-aminoethyl ether)-N,N,N',N'-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the specimen to be characterized with respect to expression level (see, for example, Ausubel et al., *Current Protocols in Molecular Biology* (Supplement 47), John Wiley & Sons, New York (1999); Harlow and Lane, *Antibodies: A Laboratory Manual* (Cold Spring Harbor Laboratory Press (1988); Harlow and Lane, *Using Antibodies: A Laboratory Manual*, Cold Spring Harbor Press (1999); *Tietz Textbook of Clinical Chemistry*, 3rd ed., Burtis and Ashwood, eds., W.B. Saunders, Philadelphia, (1999)).

If desired, the specimen can be incubated or processed in a manner to increase the availability of molecules in the specimen for analytical methods disclosed herein, including binding to a target. For example, if the molecule to be detected in the specimen is a nucleic acid and the target ligand is a nucleic acid, the specimen can be incubated in buffers and under conditions useful for preserving nucleic acids, particularly mRNA, and for detecting hybridization between nucleic acid molecules. Such conditions are well known to those skilled in the art (Sambrook et al., *Molecular Cloning: A Laboratory Manual*, 2nd ed., Cold Spring Harbor Press, Plainview, N.Y. (1989); Ausubel et al., *Current Protocols in Molecular Biology* (Supplement 47), John Wiley & Sons, New York (1999)). Furthermore, a specimen containing mRNA can be converted to cDNA, if desired, using reverse transcriptase.

A specimen can also be processed to eliminate or minimize the presence of interfering substances. For example, a specimen containing nucleic acids can be fractionated or extracted to remove potentially interfering non-nucleic acid molecules. The specimen can also be treated to decrease interfering nucleic acids, for example, by treating a specimen with DNase or RNase to increase the ability to detect RNA or DNA, respectively. Various methods to fractionate a fluid specimen or cell extract are well known to those skilled in the art, including subcellular fractionation or chromatographic techniques such as ion exchange, hydrophobic and reverse phase, size exclusion, affinity, hydrophobic charge-induction chromatography, and the like (Ausubel et al., supra, 1999; Scopes, *Protein Purification: Principles and Practice*, third edition, Springer-Verlag, New York (1993); Burton and Harding, *J. Chromatogr. A* 814:71-81 (1998)).

If the molecule to be detected in the specimen is a polypeptide and the target ligand is an antibody, the specimen can be incubated in buffers suitable for immunological detection methods, for example, the addition of detergents, including denaturants such as sodium dodecyl sulfate (SDS), if desired (Harlow and Lane, supra, 1988; Harlow and Lane, supra, 1999). The specimen can also be fractionated, for example, into cellular or subcellular fractions, if desired.

Bodily fluid specimens are particularly useful in methods of the invention due to ready availability. A particularly useful fluid specimen is a blood specimen, particularly one containing leukocytes (WBCs). A specimen from an individual containing leukocytes is representative of the physiological state of the individual and, therefore, is useful in determining the expression level of molecules in an individual that is indicative of the health state of the individual. Gene and cellular expression in leukocytes reflects many physiological systems and states in the cell, for example, nervous, immune, cardiovascular, gastrointestinal, endocrine, hepatic, lymphatic, neuromuscular, renal, respiratory, skeletal, and urogenital systems. Pathologies in these systems and perturbations in organs of these systems are reflected in the leukocytes. Therefore, using an analytical method that is useful for detecting molecules in a leukocyte specimen from an individual is particularly useful in methods of the invention. For example, a target that reflects expression of molecules in leukocytes, for example, a target containing leukocyte ESTs, can be used to determine expression in leukocytes.

Furthermore, expression in leucocytes can be used to correlate changes in expression associated with other physiological systems such as the cardiovascular system, nervous system, or other systems, as disclosed herein. Since leukocytes reflect the physiological state in a variety of systems, leukocytes can be used as a specimen to determine whether there is a change in the health state of the individual, including changes in one or more physiological systems associated with a disease or changes that are associated with a physiological change such as drinking or drug intake, and the like.

Moreover, leukocytes can also be used to detect infectious disease due to alterations in the physiological state of the individual. In addition, other physiological changes, including changes due to exercise, age, consumption of alcoholic beverages or intake of drugs are also reflected in leukocytes. Thus, a specimen containing leukocytes is convenient for determining an expression profile that can be correlated with the health state of an individual for a variety of physiological conditions, including exercise, age, drinking, and the like, in addition to disease states without the need for invasive biopsy procedures to obtain samples of tissues or organs that are directly involved in the disease.

When using leukocytes as a specimen, a serum specimen from an individual containing leukocytes can be fractionated to isolate leukocytes, if desired, or subfractionated, for example, into macrophages, T cells, B cells, granuolocytes, monocytes, neutrophils, eosinophils, basophils, mast cells, and the like. Serum can be fractionated into a leukocyte fraction or subfractionated using methods well known in clinical chemistry and blood analysis. Leukocytes or subfractions thereof can also be isolated by affinity binding methods specific for leukocytes or leukocyte subfractions. For example, an antibody binding step using a leukocyte-specific antibody can be used to isolate leukocytes. The leukocytes can optionally be eluted from the affinity matrix, or the bound leukocytes can be directly used by lysing the leukocytes bound to the affinity matrix. Similarly, antibodies specific for leukocyte subfractions such as T cell or B cell specific antibodies can be used to subfractionate leukocytes. In addition, antibodies specific to cell surface markers such as CD markers can be used to identify and/or isolate a subpopulation of cells. Such cell surface markers can also be used to determine the ratios of particular cell types in a specimen, for example, using a cell sorting apparatus, which can also be an indication of a disease state, a predisposition to developing a disease, or to determine the outcome of a disease.

In one embodiment, a direct quantitation method is used to determine the level of expression of a molecule in a specimen. One such method is the isotope-coded affinity tag (ICAT) method (Gygi et al., *Nature Biotechnol.* 17:994-999 (1999) which is incorporated herein by reference). The ICAT method is particularly useful for proteomics-based applications. The ICAT method uses an affinity tag that can be differentially labeled with an isotope that is readily distinguished using mass spectrometry, for example, hydrogen and deuterium. The ICAT affinity reagent consists of three elements, an affinity tag, a linker and a reactive group.

One element of the ICAT affinity reagent is an affinity tag that allows isolation of peptides coupled to the affinity reagent by binding to a cognate binding partner of the affinity tag. A particularly useful affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the ICAT affinity reagent.

A second element of the ICAT affinity reagent is a linker that can incorporate a stable isotope. The linker has a sufficient length to allow the reactive group to bind to a specimen polypeptide and the affinity tag to bind to its cognate binding partner. The linker also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the linker so long as the heavy and light forms can be distinguished using mass spectrometry. Exemplary linkers include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999). One skilled in the art can readily determine any of a number of appropriate linkers useful in an ICAT affinity reagent that satisfy the above-described criteria.

The third element of the ICAT affinity reagent is a reactive group, which can be covalently coupled to a polypeptide in a specimen. Any of a variety of reactive groups can be incorporated into an ICAT affinity reagent so long as the reactive group can be covalently coupled to a specimen molecule. For example, a polypeptide can be coupled to the ICAT affinity reagent via a sulfhydryl reactive group, which can react with free sulfhydryls of cysteine or reduced cystines in a polypeptide. An exemplary sulfhydryl reactive group includes an iodoacetamido group, as described in Gygi et al. (supra, 1999). Other examplary sulfhydryl reactive groups include maleimides, alkyl and aryl halides, α-haloacyls and pyridyl disulfides. If desired, the specimen polypeptides can be reduced prior to reacting with an ICAT affinity reagent, which is particularly useful when the ICAT affinity reagent contains a sulfhydryl reactive group.

A reactive group can also react with amines such as Lys, for example, imidoesters and N-hydroxysuccinimidyl esters. A reactive group can also react with carboxyl groups found in Asp or Glu, or the reactive group can react with other amino acids such as His, Tyr, Arg, and Met. Methods for modifying side chain amino acids in polypeptides are well known to those skilled in the art (see, for example, Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). One skilled in the art can readily determine conditions for modifying specimen molecules by using various reagents, incubation conditions and time of incubation to obtain conditions optimal for modification of specimen molecule for use in methods of the invention.

The ICAT method is based on derivatizing a specimen molecule such as a polypeptide with an ICAT affinity reagent. A control reference specimen and a specimen from an individual to be tested are differentially labeled with the light and heavy forms of the ICAT affinity reagent. The derivatized specimens are combined and the derivatized molecules cleaved to generate fragments. For example, a polypeptide molecule can be enzymatically cleaved with one or more proteases into peptide fragments. Exemplary proteases useful for cleaving polypeptides include trypsin, chymotrypsin, pepsin, papain, *Staphylococcus aureus* (V8) protease, and the like. Polypeptides can also be cleaved chemically, for example, using CNBr or other chemical reagents.

Once cleaved into fragments, the tagged fragments derivatized with the ICAT affinity reagent are isolated via the affinity tag, for example, biotinylated fragments can be isolated by binding to avidin in a solid phase or chromatographic format. If desired, the isolated, tagged fragments can be further fractionated using one or more alternative separation techniques, including ion exchange, reverse phase, size exclusion affinity chromatography and the like. For example, the isolated, tagged fragments can be fractionated by high performance liquid chromatography (HPLC), including microcapillary HPLC.

The fragments are analyzed using mass spectrometry (MS). Because the specimen molecules are differentially labeled with light and heavy affinity tags, the peptide fragments can be distinguished on MS, allowing a side-by-side comparison of the relative amounts of each peptide fragment from the control reference and test specimens. If desired, MS can also be used to sequence the corresponding labeled peptides, allowing identification of molecules corresponding to the tagged peptide fragments.

An advantage of the ICAT method is that the pair of peptides tagged with light and heavy ICAT reagents are chemically identical and therefore serve as mutual internal standards for accurate quantification (Gygi et al., supra, 1999). Using MS, the ratios between the intensities of the lower and upper mass components of pairs of heavy- and light-tagged fragments provides an accurate measure of the relative abundance of the peptide fragments. Furthermore, a short sequence of contiguous amino acids, for example, 5-25 residues, contains sufficient information to identify the unique polypeptide from which the peptide fragment was derived (Gygi et al., supra, 1999). Thus, the ICAT method can be conveniently used to identify differentially expressed molecules, if desired.

The ICAT method can be used to quantitate the expression levels of molecules in reference individuals. Because the ICAT method is based on a direct comparision between two samples, the expression levels in various reference individuals can be conveniently quantitated relative to the same control reference specimen, for example, another reference individual or an appropriate cell line. Thus, the ICAT method can be conveniently used to quantitate the expression levels of molecules in reference individuals to determine a health-associated reference expression region.

Furthermore, the ICAT method can be used to quantitate the expression levels of molecules in an individual to be tested for his or her health state. The expression levels of molecules in a test individual can be compared to reference expression levels. For example, the reference expression levels can be those of a control reference specimen, which are directly compared to the test individual using differential isotope labeling in the ICAT method. The control reference specimen can be the same as that used to determine the health-associated reference expression region. Alternatively, the control specimen can be different than that used to establish the health-associated reference expression region, so long as the expression levels of the control reference specimen is correlated with the health-associated reference expression region.

The control reference specimen can also be a pool of reference specimens. For example, the control reference specimen can be a pool of two or more specimens of reference individuals used to establish a health-associated reference region and can be a pool of all reference individuals, if desired. Such a pool of all reference individuals is expected to result in a reference level that is essentially an average of the reference individuals. One skilled in the art can readily determine a desired number of one or more reference individuals, including all reference individuals, to include in a pool for use as a control reference specimen. The amount of a pooled sample is adjusted accordingly to allow direct comparison to the test individual, for example, based on cell number, amount of protein, or some other appropriate measure of the relative amount of control reference specimen and test specimen.

The above-described ICAT method can be performed as tandem MS/MS. A dual mode of MS can be performed in which MS alternates in successive scans between measuring relative quantities of peptides and recording of sequence information of selected peptides (Gygi et al., supra, 1999). Other modes of MS include matrix-assisted laser desorption-time of flight (MALDI-TOF), an electrospray process with MS, and ion trap. In ion trap MS, fragments are ionized by electrospray and then put into an ion trap. Trapped ions can then be separately analyzed by MS upon selective release from the ion trap. Fragments can also be generated in the ion trap and analyzed.

In addition to polypeptides, the ICAT method can similarly be applied to determining the expression level of nucleic acid molecules. In such a case, the ICAT affinity reagent incorporates a reactive group for a nucleotide, for example, a group reactive with an amino group. The ICAT affinity reagent can incorporate functional groups specific for a particular nucleotide or a nucleotide sequence of 2 or more nucleotides. The nucleic acid molecules can be cleaved enzymatically, for example, using one or more restriction enzymes, or chemically (see Sambrook et al., supra, 1989; Ausubel et al., supra, 1999).

In another embodiment, a binding assay is used to determine the expression level of a specimen molecule. For example, molecules in a specimen from the individual is contacted with a target. The target contains ligands, which can be essentially any type of molecule such as polypeptide, nucleic acid, carbohydrate, lipid, or any organic derived compound, so long as the ligand can bind to a molecule that is representative of the expression profile corresponding to one or more molecules in a specimen. The choice of target ligand depends on which type of molecule in the specimen is to be detected.

For example, a target ligand useful for detecting nucleic acids such as mRNA in a specimen can be a nucleic acid. In such a target, the ligands are representative of mRNAs expressed in a specimen and include ligands that can bind a sample of molecules predictive of the health state of an individual. A target can contain nucleic acid ligands that are representative of each mRNA in a specimen, or a target can contain nucleic ligands that are representative of a subset of mRNAs expressed in a specimen so long as the number and representation of target ligands are sufficient to generate an expression profile useful for determining the health state of an individual. A target containing nucleic acid ligands representative of relatively low abundance or rare mRNAs in a specimen is particularly useful when such low abundance mRNAs vary with the health state of an individual. The number of ligands to include in a target can be readily determined by one skilled in the art depending on the particular application and number of specimen molecules desired to be detected.

A target containing nucleic acid ligands allows determination of the expression profile of nucleic acid molecules such as mRNA in a specimen. The nucleic acid ligands can be DNA or RNA and can be oligonucleotides. A target nucleic acid can also be peptide-nucleic acid molecules (PNA) having peptide and nucleic acid molecules covalently bound (Nielson, Current Opin. Biotechnol. 10:71-75 (1999)).

A target containing nucleic acid ligands can also be used to determine the expression level of nucleic acid-binding polypeptides. Detection of nucleic acid-binding polypeptides can be particularly useful if changes in expression of nucleic acid-binding polypeptides, for example, transcription factors, is associated with a disease or predisposition to developing a disease. Target nucleic acid ligands can additionally be aptamers that bind to specimen polypeptide molecules. Aptamers are oligonucleotides having binding affinity for polypeptides (Tuerk and Gold, Science 249:505-510 (1990); Ellington and Szostak, Nature 346:818-822 (1990); Joyce, Curr. Opin. Struct. Biol. 4:331-336 (1994); Gold et al., Annu. Rev. Biochem. 64:763-797 (1995); Jayasena, Clin. Chem. 45:1628-1650 (1999); Famulok and Mayer, Curr. Top. Microbiol. Immunol. 243:123-136 (1999)). A diversity of at least $10^{15}$ species can be synthesized. For example, DNA apatamers can be synthesized with variable nucleic acid sequences flanked on each end by recognition sites for PCR primers. If desired, apatamers that bind to a polypeptide can be selected and amplified, and such apatamers can have affinities greater than antibodies.

Nucleic acid ligands of the target are chosen based on the desired specimen molecules to be detected. For example, if a known subset of specimen nucleic acids is to be detected, the target nucleic acids can correspond to specific nucleic acid sequences that can hybridize to the known subset of specimen nucleic acids. Similarly, if a known set of nucleic acid-binding polypeptides is to be detected in the specimen, the nucleic acid ligands can be nucleic acid sequences that function as binding sites for the nucleic acid-binding polypeptides. Alternatively, the target nucleic acid ligands can be representative of expressed sequence tags (ESTs) corresponding to a particular cell type. For example, if the specimen from the individual is a leukocyte, the sequences of the target ligands can correspond to ESTs representative of the expression pattern in a leukocyte. In such a case, the ESTs of a specimen comprising a cell such as a leukocyte can be known, or a target can contain EST sequences where each individual sequence is not necessarily known. Furthermore, a target containing ESTs can be analyzed with respect to the expression of particular ESTs in various physiological systems such as the cardiovascular system, the nervous system and the like. ESTs expressed in particular systems can be selected as potential sample molecules useful in determining changes in the health state of an individual affecting particular systems.

Additionally, the target nucleic acid ligands can be completely random sequences such as random oligonucleotide sequences, which can be generated by degenerate synthetic schemes. Random oligonucleotide sequences can be used as target ligands so long as the target contains a sufficient number of random nucleotide sequences that are statistically representative of a sufficient number of specimen molecules to provide a useful expression profile. One skilled in the art can readily select appropriate nucleic acid ligands based on the particular application and the specimen molecules to be detected so long as the target provides a sufficient number of target ligands to determine an expression profile of an individual.

A target useful for detecting polypeptides in a specimen can contain ligands that specifically bind to the polypeptides. Target ligands useful for detecting polypeptides include nucleic acids, as described above, antibodies, peptides or small molecule ligands such as small organic molecules. Antibody ligands are particularly useful for detecting polypeptides in a specimen, including various biochemical forms of a polypeptide such as post-translational modifications and the presence or absence of post-translational modifications. Antibodies can be designed, for example, to detect the presence or absence of phosphorylation at one or more sites of phosphorylation.

Methods for preparing antibodies for use as target ligands are well known to those skilled in the art. As used herein, the term "antibody" is used in its broadest sense to include polyclonal and monoclonal antibodies, as well as antigen binding fragments of such antibodies. An antibody useful in the invention, or antigen binding fragment of such an antibody, is characterized by having specific binding activity for a polypeptide or a peptide portion thereof of at least about $1 \times 10^5$ M$^{-1}$. Thus, Fab, F(ab')$_2$, Fd, Fv, single chain Fv (scFv) fragments of an antibody and the like, which retain specific binding activity for a polypeptide, are included within the definition of an antibody. Specific binding activity of an antibody for a polypeptide can be readily determined by one skilled in the art, for example, by comparing the binding activity of an antibody to a particular polypeptide versus a control polypeptide that is not the particular polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making functional antibodies are well known to those skilled in the art (Winter and Harris, *Immunol. Today* 14:243-246 (1993); Ward et al., *Nature* 341: 544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

Antibody ligands useful in methods of the invention can be generated having specificity for known specimen polypeptides, as described above. A particularly useful method for generating antibody ligands is based on using combinatorial libraries consisting of variable heavy chains and variable light chains (Huse et al., *Science* 246:1275-1281 (1989)). The advantage of using such a combinatorial antibody library is that antibodies do not have to be individually generated for each specimen molecule to be detected. No prior knowledge of the exact characteristics of molecules in a specimen is required when using a combinatorial antibody library. All that is necessary is that a sufficient number of antibody ligands be included in the target so that a representative number of specimen molecules can be detected and that a useful expression profile of an individual can be determined. If desired, an antibody library can be screened for binding to molecules expressed in a specimen, for example, by selecting for antibodies that bind to specimen molecules such as molecules expressed in leukocytes. The selected antibodies can be used as target ligands for binding to specimen molecules.

In addition to antibody ligands, organic molecule ligands, including peptides, can be used to detect molecules in a specimen. Such organic molecule ligands can be conveniently generated using combinatorial chemistry methods. Methods for producing pluralities of compounds to use as target ligands, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art (see, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)). When a library of peptides is used as ligands for detecting specimen polypeptides, the peptides can form into functional domains having binding activity to specimen polypeptides. Libraries containing large numbers of natural and synthetic compounds also can be obtained from commercial sources. Because a large number and variety of ligands can be generated by such combinatorial methods, a target containing organic molecule ligands can be readily prepared and used to determine the expression profile of an individual.

Target ligands can be attached to a solid support for contacting with a specimen, or the target ligands can be in solution and contacted with a specimen. Generally, target ligands are stably bound to a solid support, which can be a membrane such as a nylon or nitrocellulose membrane, glass, derivatized glass, silicon, plastic or other substrates. The target molecules can be bound to a flat surface such as a membrane or plate or can be bound to spheres or beads. Alternatively, specimen molecules can be bound to a solid support and contacted with target ligands in solution.

A convenient format for a target can be, for example, an array containing a plurality of ligands such as nucleic acids, antibodies, peptides or small organic molecules. As used herein, an array refers to a format for presenting binding molecules where the ligands are stably bound to a solid support and arranged such that the binding to a particular ligand on the array can be detected. An array format is particularly convenient when a large number of molecules in a specimen is desired to be detected. For example, a target containing nucleic acid ligands can be an array of random oligonucleotides or an array of ESTs. Such nucleic acid arrays can be purchased commercially or custom synthesized. Similarly, ligands such as antibodies, peptides or small organic molecules can be attached to a solid support in an array format.

The target ligands can be stably bound to a solid support via covalent interactions or non-covalent interactions so long as the ligands remain bound to the solid support during incubation or wash steps required to detect specific binding of a specimen molecule to the target. Generally, target ligands are attached to a solid support, for example, through covalent bonds such as chemical crosslinks. A ligand can also be modified with an affinity tag that facilitates binding and or crosslinking of the ligand to the solid support. High affinity non-covalent interactions such as those mediated by avidin and streptavidin and the like can also be used to stably bind a ligand to a solid support.

It is understood that a target, as used herein, refers to the total number of different ligands used to detect molecules in a specimen. For example, if the diversity of ligands required to determine the expression profile of an individual requires the use of three individual arrays each containing different ligands, the target is considered to be the ligands on all three arrays. Moreover, it is understood that contacting a specimen with a target contained on multiple arrays can be performed simultaneously, sequentially, or even at different times, for example, on different days or weeks or even months apart so long as appropriate conditions are used to allow comparison of the binding interactions, as described below.

The specimen is contacted with the target under conditions that allow specific binding of the specimen molecules to the target ligands. As used herein, specific binding means binding that is measurably different from a non-specific interaction. Specific binding can be measured, for example, by determining binding of a molecule compared to binding of a control molecule, which generally is a molecule of similar structure that does not have binding activity, for example, a peptide of similar size that lacks binding activity or a nucleic acid having a different nucleotide sequence. Specificity of binding also can be determined, for example, by competition with a control molecule, for example, competition with an excess of the same molecule. In this case, specific binding is indicated if the binding of a molecule is competitively inhibited by itself.

The conditions for the contacting step of a specimen and target can vary depending on the particular type of specimen molecule and target ligand. The nature of the desired binding interaction between specimen molecule and target ligand and the method used to detect specific binding is also considered when determining appropriate binding conditions. For example, if the specimen molecule is a nucleic acid and the target ligand is a nucleic acid, the contacting step is carried out under conditions that allow specific binding and detection of specific binding. Such methods are well known to those skilled in the art, as described above (Sambrook et al., supra, 1989; Ausubel et al., supra, 1999). Typically, the binding interaction between specimen nucleic acids and target nucleic acid ligands are carried out under conditions that allow specific hybridization between specimen molecules and target ligands. In such a case, the target ligands generally are single stranded nucleic acid molecules that can hybridize to the specimen molecules. In contrast, if the specimen molecule is a nucleic acid-binding polypeptide such as a transcription factor and the target ligand is a nucleic acid, the target ligands can be double stranded nucleic acids since nucleic acid-binding molecules such as transcription factors often bind to double stranded DNA. One skilled in the art can readily determine the appropriate biochemical form of target ligands, for example, single stranded or double stranded nucleic acid, and conditions for specific binding of specimen molecules depending on the particular binding interaction to be detected.

The methods of the invention include the step of comparing the expression levels of molecules in a specimen from an individual with a health-associated reference expression region. Although not required, the health-associated reference expression region for the molecules is generally determined prior to determining the expression levels of molecules in a specimen from a non-reference individual, that is, a test individual. Furthermore, it is possible that the expression level of one molecule in a specimen is determined at a different time than the determination of the expression level of a second molecule in a specimen. Whether the expression level of a molecule is determined simultaneously with the determination of an expression level for a second molecule in a specimen or the determination of a health-associated reference expression region of the molecules, it is understood that such determinations are made under conditions that allow a statistically useful comparison, even if obtained at different times.

One useful method to allow comparison between specimens analyzed at different times is to use an internal control that can be used to normalize results between specimens. A particularly useful internal control can be, for example, a molecule in the specimen for which the expression level does not significantly vary between a reference health state and a perturbed health state. An internal control molecule can be a molecule corresponding to or encoding molecules such as actin, other cytoskeletal proteins, or any polypeptide or encoding nucleic acid that does not significantly vary between a reference health state or a perturbed health state such as a disease state. Alternatively or in addition, an exogenous control molecule can be added to normalize variability between specimens collected at different times or from different individuals.

The use of internal and exogenous controls allows determination of the reproducibility of specimen collection and analysis. One skilled in the art will know or can readily determine if the expression level determined for a molecule, whether in a population of reference individuals for obtaining a health-associated reference expression region or in an individual for determining an individual expression profile, is reproducible and reliable for use in methods of the invention based on statistical analysis and determination of experimental variability.

The binding of a specimen molecule to a target ligand can be detected using well known methods and is based on the particular type of specimen molecule and target ligand binding interaction to be detected. For example, a specimen molecule or target ligand can be modified to include a detectable moiety, for example, a radiolabel, a fluorochrome, a chromogen, a ferromagnetic substance, a luminescent tag, a detectable binding agent such as biotin, an enzyme such as horse radish peroxidase (HRP), alkaline phosphatase, glucose oxidase, and the like, or other detectable moieties known in the art that are detectable by analytical methods. Methods suitable for detecting such moieties include, for example, autoradiography or phosphorimaging, fluorescence spectroscopy, colorimetric detection, or light detection.

As used herein, a label refers to single atoms and molecules that are either directly or indirectly involved in the production of a detectable signal. Any label can be linked to target ligands or to specimen molecules. These detectable atoms or molecules can be used alone or in conjunction with additional reagents. Such additional reagents are well-known in clinical diagnostic chemistry. The linking of a label to a substrate, for example, a specimen molecule or target ligand, including nucleic acid, polypeptides, antibodies, and small organic molecules, is well known in the art. For example, in the case of nucleic acids, nucleotides labeled with radioactive, fluorescent, or colorimetric moieties can be incorporated enzymatically or chemically into a nucleic acid. In the case of specimen polypeptides, polypeptides can be modified by conjugating a detectable moiety with a chemical cross linking agent or metabolically labeling cells in a specimen to incorporate a radiolabel. As described above, an isotopic label such as an ICAT affinity reagent can also be conjugated to a specimen molecule and detected by MS. Antibodies can be labeled by conjugating detectable labels, including enzymes, using cross linking agents or, if the antibodies are expressed recombinantly, for example, using antibody libraries, the antibodies can be labeled by expressing the antibodies as a fusion with a detectable peptide tag.

A method of detection that directly measures binding of a specimen molecule to a target ligand can also be used. In such a case, the binding of a specimen molecule to a target ligand is performed without either the specimen molecules or target ligands being directly labeled. Such indirect methods include using mass spectrometry or detectable secondary reagents that bind to a specimen molecule or target ligand.

The choice of detection system will depend on the nature of the specimen molecule and target ligand binding interaction. For example, a variety of detection systems can be used if a specimen nucleic acid molecule is to be detected. Such methods include specific hybridization and/or amplification methods. Methods and conditions for hybridizing a specimen nucleic acid molecule to a target nucleic acid ligand are well known to those skilled in the art. Hybridization conditions can vary depending on the stringency of the binding and washing conditions. Hybridization reactions can be performed under low stringency, moderate stringency, or high stringency conditions. The conditions for various stringency hybridization reactions are well known to those skilled in the art (see Sambrook et al., supra, 1989; Ausubel et al., supra, 1999).

The phrase stringent hybridization is used herein to refer to conditions under which polynucleic acid hybrids are stable. Typically, the hybridization reaction is performed under conditions of lower stringency, followed by washes of varying, but higher, stringency. Reference to hybridization stringency relates to such washing conditions.

The phrase "moderately stringent hybridization" refers to conditions that permit target-nucleic acid to bind a complementary nucleic acid. The hybridized nucleic acids will generally have at least about 60% identity, at least about 75% identity, more at least about 85% identity; or at least about 90% identity. Moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C.

High stringency hybridization refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd ed., Cold Spring Harbor Press, Plainview, N.Y. (1989); and Ausubel et al., supra, (1999).

If desired, a specimen nucleic acid can be amplified using methods such as polymerase chain reaction (PCR). If the specimen nucleic acid is RNA, the RNA molecules can be reverse transcribed into cDNA. Methods of amplifying nucleic acids by PCR and reverse transcription are well known to those skilled in the art (see, for example, Dieffenbach and Dveksler, *PCR Primer: A Laboratory Manual*, Cold Spring Harbor Press (1995); Ausubel et al., supra, 1999).

To detect binding of a specimen nucleic acid molecule to a target ligand, the specimen molecules can be labeled with a detectable moiety such as a radiolabel, fluorescent label, or colorimetric label. When specimen mRNA is to be detected, a detectable moiety can be incorporated, for example, during reverse transcription of the mRNA into cDNA. Alternatively, the target ligand can be labeled to detect binding of a specimen molecule, for example, the target ligand can be labeled with a fluorescent label that is quenched upon binding of a nucleic acid molecule. Another system is the molecular beacon system in which the target ligand contains a fluorescent label and a quencher such that a fluorescent signal is emitted upon hybridization to a specimen molecule (Fang et al., *J. Am. Chem. Soc.* 121:2921-2922 (1999); Fang et al., *SPIE*, 3602: 149-155 (1999)). Furthermore, methods in which neither the specimen molecule nor the target ligand is labeled can also be used to detect a binding interaction between a specimen nucleic acid molecule and target nucleic acid ligand, for example, mass spectrometry.

Alternatively, a secondary reagent that is detectably labeled can be used to detect binding of nucleic acids. For example, a specimen containing nucleic acid molecules can be hybridized to target nucleic acid ligands, and unbound specimen molecules can be removed. The target can then be contacted with secondary reagent nucleic acids containing a detectable moiety such as a radiolabel, fluorescent label, or colorimetric label. Those target nucleic acid ligands that are bound to specimen nucleic acid molecules are inaccessible to the labeled secondary reagent nucleic acids whereas the secondary reagent can bind to unbound target nucleic acid ligands, allowing detection of binding interactions.

For detection of binding of a specimen polypeptide to a target antibody ligand, the detection methods can employ a labeled specimen polypeptide, a labeled target antibody ligand, or a labeled secondary reagent, similar to the methods described above for detecting nucleic acid binding. For example, the specimen polypeptides can be metabolically radiolabeled, or a detectable moiety such as a radiolabel, fluorescent, or colorimetric label can be attached to specimen polypeptides by enzymatic or chemical means. Alternatively, a target antibody ligand can be labeled, or binding of a target antibody ligand to a specimen molecule can be detected using well known immunological detection methods (Harlow and Lane, supra, 1988; Harlow and Lane, supra, 1999). Methods of detecting binding of a target antibody ligand using well known immunological methods are particularly useful when the specimen molecules are attached to a solid support.

Methods of detecting binding of a specimen polypeptide to a target antibody ligand can also employ methods in which neither the specimen polypeptide nor the target antibody ligand are detectably labeled, for example, using mass spectrometry. Additionally, a labeled secondary reagent can be used to detect binding interactions between a specimen polypeptide and a target antibody ligand similar to the methods described above for detecting nucleic acid binding. For example, a specimen containing polypeptide molecules can be contacted with target antibody ligands, and unbound specimen molecules can be removed. The target can then be contacted with labeled secondary reagents containing a detectable moiety such as a radiolabel, fluorescent, or colorimetric label and that can bind to unbound antibodies but not to antibodies bound to specimen polypeptides. Those target antibody ligands that are bound to specimen polypeptide molecules are inaccessible to the labeled secondary reagents whereas the labeled secondary reagents can bind to unbound target antibody ligands, allowing detection of binding interactions.

Detection of specimen polypeptide molecules bound to target nucleic acid ligands can also be based on differential staining of polypeptides. The use of protein stains to detect binding of polypeptides to nucleic acids can be particularly useful when detecting binding of polypeptides to aptamers.

Alternatively, laser bombardment can be used to detect binding of specimen polypeptides to target ligands.

The methods of the invention are based on determining the expression levels of molecules in a specimen or specimens to determine a health-associated reference expression region or to determine the expression profile of an individual to compare to a health-associated reference expression region. Therefore, the methods involve quantitation of the expression of molecules in a specimen. Methods for quantitative assays of the expression level of a specimen molecule are well known to those skilled in the art. For example, if desired, the target can contain various amounts of a ligand to facilitate quantitation of binding of a specimen molecule.

Furthermore, a target can contain different amounts of target ligands suitable for quantitating expression levels of specimen molecules based on expected expression ranges of the specimen molecules. Such expected ranges can be determined using target-based methods, for example, using arrays. Alternatively, quantitation of expression levels can be performed by another method, for example, using a direct method such as ICAT, and correlated with a target-based method such as an array. Thus, quantitation by a method such as ICAT can be used to establish expected expression ranges of molecules and to calibrate a target-based method for convenient use in an array format. Thus, the amount of different ligands on the target need not be identical and can be varied to provide optimized detection of molecules in a specimen.

Methods for determining the levels of expression of small molecules are well known to those skilled in the art. For example, methods of analyzing small molecules such as glucose, sugars, carbohydrates, sodium, potassium, chloride, calcium, chromium, iron, selenium, magnesium, manganese, molybdenum, zinc, copper, amino acids, lipids, neurotransmitters such as acetylcholine, dopamine, norepinephrine, epinephrine, seratonin, γ-aminobutyrate, and the like, as well as other small molecules disclosed herein, can be analyzed using well known clinical chemistry methods (see, for example, *Tietz Textbook of Clinical Chemistry*, second edition, Burtis and Ashwood, eds., W.B. Saunders Company, Philadelphia (1994); *Tietz Textbook of Clinical Chemistry*, 3rd ed., Burtis and Ashwood, eds., W.B. Saunders Co., Philadelphia (1999)).

The methods of the invention disclosed herein for detecting nucleic acids and/or polypeptides, particularly methods useful for detecting large numbers of molecules such as array-based methods, can be combined with well known methods of detecting expression levels of small molecules to determine the expression levels of more than one type of molecule. Examplary methods of determining the levels of small molecules include the use of enzyme-based assays, including colorimetric and radioenzymatic (incorporation of radioactive substrates), chromogenic assays, spectrophotometry, fluorescence spectroscopy, liquid chromatography, including ion exchange, affinity, HPLC, paper chromatography, gas chromatography, photometry atomic absorption spectrometry, emission spectroscopy, including inductively coupled plasma emission spectroscopy, mass spectrometry, inductively coupled mass spectrometry, neutron activation analysis, X-ray fluorescence spectrometry, electrochemical techniques such as anodic stripping voltametry, polarographic techniques, flame emission spectrophotometry, electrochemical methods such as ion selective electrodes, chemical titration, and the like (*Tietz Textbook of Clinical Chemistry*, second edition, Burtis and Ashwood, eds., W.B. Saunders Company, Philadelphia (1994); *Tietz Textbook of Clinical Chemistry*, 3rd ed., Burtis and Ashwood, eds., W.B. Saunders Co., Philadelphia (1999)). Small molecule assay methods can also be adapted to accommodate multiple samples, including solid phase or array based formats.

Additional methods to those described above for measuring the expression levels of molecules in a sample can be used. Any new methods can be correlated with a previously determined method that is useful for determining the expression levels of molecules in a sample. Once a data set has been determined, for example, a sample of molecules correlated with a disease has been identified and a health-associated reference expression region has been determined by a particular method, the previously used method can be correlated with a new set of molecules or method of assaying the expression levels of the molecules. For example, the expression of molecules can be measured using the old method and compared to a new method. By comparing the old and new methods using a calibration curve, the information determined by the old method can be transformed and correlated with a new method for measuring the expression of molecules in a sample. The transformed method is validated by correlating data derived by the two methods. If transformation does not provide a good correlation between the two methods, the new method can be validated by generating a new set of calibrations for the new method.

The methods of the invention described herein can also be used to diagnose a disease or condition in an individual. The invention thus provides a method of diagnosing a disease. The method of diagnosing a disease can include the step of comparing the expression levels of a sample of molecules in a population of molecules in a specimen from an individual with health-associated reference expression intervals of the molecules in the sample, wherein an expression level within the health-associated reference expression intervals indicates a reference health state and wherein an expression level outside the health-associated reference expression interval indicates a disease state.

In addition, the method of diagnosing a disease can include the step of determining a multidimensional coordinate point representative of the expression levels of a sample of molecules in a population of molecules in a specimen from the individual; comparing the multidimensional coordinate point to a health-associated reference expression region of the sample of molecules; and determining if the multidimensional coordinate point is within or outside the health-associated reference expression region, wherein the multidimensional coordinate point within the health-associated reference expression region indicates a reference expression profile and wherein the multidimensional coordinate point outside the health-associated reference expression region indicates a perturbed expression profile.

The methods can further include the step of determining the expression levels of a sample of molecules in a population of molecules in the specimen. The method can also include the step of contacting a specimen from an individual with a target or directly comparing the expression levels of molecules with reference expression levels correlated with a health-associated reference expression region.

The methods of the invention can be used to determine the health state of an individual and to diagnose a variety of diseases. The methods of the invention can be used to diagnose diseases, for example, cancer, including breast, prostate, ovarian, lung colorectal, hepatic, renal, leukemia, and lymphoma; cardiovascular diseases, including heart failure, hypertension and atherosclerosis; respiratory diseases; renal diseases; gastrointestinal diseases, including inflammatory bowel diseases such as Crohn's disease and ulcerative colitis; hepatic, gallbladder and bile duct diseases, including hepatitis and cirrhosis; hematologic diseases; metabolic diseases;

endocrine and reproductive diseases, including diabetes; bone and bone mineral metabolism diseases; immune system diseases, including autoimmune diseases such as rheumatoid arthritis, lupus erythematosus, and other autoimmune diseases; musculoskeletal and connective tissue diseases, including arthritis; infectious diseases; and neurological diseases.

In addition to diagnosing various diseases, the methods of the invention can also be used to determine the health state of an individual as it relates to the physiological state of the individual. For example, the health state of an individual can be determined to indicate if the individual has consumed alcoholic beverages or drugs, has been exercising, or other physiological changes that result in changes in the expression profile of an individual relative to a reference population.

The invention additionally provides a method of diagnosing a health state in an individual. The method of diagnosing a health state can include the steps of determining the expression levels of a sample of molecules in a population of molecules in a specimen from an individual; comparing the expression levels with a health-associated reference expression region of the sample of molecules; and determining if the expression levels of the sample of molecules is within or outside the health-associated reference expression region, wherein expression levels within the autoimmune diseases; musculoskeletal and connective tissue diseases, including arthritis; infectious diseases; and neurological diseases.

In addition to diagnosing various diseases, the methods of the invention can also be used to determine the health state of an individual as it relates to the physiological state of the individual. For example, the health state of an individual can be determined to indicate if the individual has consumed alcoholic beverages or drugs, has been exercising, or other physiological changes that result in changes in the expression profile of an individual relative to a reference population.

The invention additionally provides a method of diagnosing a health state in an individual. The method of diagnosing a health state can include the steps of determining the expression levels of a sample of molecules in a population of molecules in a specimen from an individual; comparing the expression levels with a health-associated reference expression region of the sample of molecules; and determining if the expression levels of the sample of molecules is within or outside the health-associated reference expression region, wherein expression levels within the health-associated reference expression region indicates a reference health state and wherein expression levels outside the health-associated reference expression region indicates a disease state.

The method of diagnosing a health state can also include the steps of (a) comparing the expression level of a molecule in a specimen from the individual with a health-associated reference expression interval of the molecule; and (b) assigning a value of 0 if the expression level is within the health-associated reference expression interval or assigning a positive numerical value if the expression level is outside the health-associated reference expression interval, wherein an expression level within the health-associated reference expression interval indicates a reference health state and wherein an expression level outside the health-associated reference expression interval indicates a perturbed health state. Similarly, the expression levels can be compared to one or more health-associated reference expression regions.

Also, the method of diagnosing a health state can includes the steps of (a) comparing the expression level of a molecule in a specimen from the individual with a health-associated reference expression interval of the molecule; and (b) assigning a value of 0 if the expression level is within the health-associated reference expression interval, assigning a positive numerical value if the expression level is greater than the health-associated reference expression interval, or assigning a negative numerical value if the expression level is less than the health-associated reference expression interval, wherein a value of 0 indicates a reference health state and wherein a positive or negative numerical value indicates a perturbed health state. Similar methods can be performed comparing expression levels of a sample of molecules to a health-associated reference expression region.

In methods of the invention, the determination of the expression level(s) of a molecule or group of molecules in a specimen allows comparison to a health-associated reference expression interval for that molecule or to a health-associated reference expression region for that group of molecules. Once the expression level(s) of a molecule or group of molecules is determined, the expression level(s) can be inputted into a method for comparing the expression level of the molecule to a health-associated reference expression interval or the expression levels for the group of molecules to a health-associated reference expression region. A value can be assigned based on whether the expression level of the molecule is within or outside a health-associated reference expression interval, particularly in a one-molecule-at-a-time analysis. Methods of comparing the expression level(s) of a molecule or group of molecules in a specimen to a health-associated reference expression region and optionally assigning a value based on whether the expression level is within the health-associated reference expression region can be used to determine an expression profile based on the expression level of a few molecules to a large number of molecules in a sample so long as the number of molecules is sufficient to provide an expression profile of an individual that indicates the health state of the individual, and such information can be used to estimate the course of a disease.

The methods of the invention can be conveniently performed on a computer apparatus. Any of the methods or particular steps of the methods disclosed herein can be performed on a computer apparatus. Performing one or more steps of an invention method on a computer apparatus is particularly useful when analyzing a large number of parameters such as a large number of sample molecules.

The invention thus provides a computer apparatus comprising a processor; main memory in communication with the processor; and a comparative expression profiler in communication with the main memory configured to carrying out the computer-executed steps of (a) comparing the expression level of a molecule with a health-associated reference expression interval of the molecule; and (b) assigning a value of 0 if the expression level is within the health-associated reference expression interval or assigning a positive numerical value if the expression level is outside the health-associated reference expression interval, wherein an expression level within the health-associated reference expression interval indicates a reference expression profile and wherein an expression level outside the health-associated reference expression interval indicates a perturbed expression profile.

The invention also provides a computer apparatus comprising a processor; main memory in communication with the processor; and a comparative expression profiler in communication with the main memory configured to carrying out the computer-executed steps of (a) comparing the expression level of a molecule with a health-associated reference expression interval of the molecule; and (b) assigning a value of 0 if the expression level is within the health-associated reference expression interval, assigning a positive numerical value if the expression level is greater than the health-associated reference expression interval, or assigning a negative numerical value if the expression level is less than the health-associated reference expression interval, wherein an expression level within the health-associated reference expression interval indicates a reference expression profile and wherein an expression level outside the health-associated reference expression interval indicates a perturbed expression profile (see FIG. 1). In a computer apparatus of the invention, steps (a) and (b) can be repeated one or more times, particularly in a one-molecule-at-a-time analysis.

The invention provides a computer apparatus, comprising a processor; main memory in communication with the processor; and a comparative expression profiler in communication with the main memory configured to carrying out the computer-executed steps of: (a) determining a multidimensional coordinate point representative of the expression levels of a sample of molecules from an individual; (b) comparing the multidimensional coordinate point with a health-associated reference expression region, wherein the multidimensional coordinate point within the health-associated reference expression region indicates a reference expression profile and wherein the multidimensional coordinate point outside the health-associated reference expression region indicates a perturbed expression profile (see FIG. 7).

An invention computer apparatus can further be configured to carry out the computer-executed step of determining the expression level of the molecule. It is understood that any of the methods disclosed herein that are conveniently performed on a computer apparatus can be included as steps to be performed by an invention computer apparatus. For example, a computer based method can be used to select a sample of molecules in a population of molecules in a specimen by determining which molecules have a health-associated reference region that is statistically useful or to perform any of the statistical methods, as disclosed herein. A computer apparatus is also useful for determining a multidimensional coordinate point and comparing the coordinate point to a health-associated reference expression region. A molecule that does not have a statistically reproducible health-associated reference expression interval in a reference population can be excluded from the sample molecules by the computer based method.

The methods of the invention directed to assigning values based on whether the expression level of a molecule is within or outside a health-associated reference expression interval can be advantageously performed using a computer apparatus since the methods are directed to assigning numerical values, which can be readily processed on a computer apparatus. The use of a computer apparatus is also convenient since a health-associated reference expression interval for a large number of molecules can be conveniently stored and accessed for comparison to the expression level of a molecule from a specimen. Similarly, the methods of the invention directed to determining a multidimensional coordinate point and comparing to a health-associated reference expression region can be conveniently performed on a computer apparatus, and the computer apparatus can be used to store instructions for determining inclusion in one or more health-associated reference expression regions of various reference populations as well as a database of health-associated reference regions for comparison to a test individual.

It is understood that a computer apparatus of the invention need not itself store the health-associated reference expression interval of various molecules or a health-associated reference expression region. The computer apparatus contains a comparative expression profiler, which is capable of comparing an expression level of a molecule to a health-associated reference expression interval or expression levels for a group of molecules to a health-associated reference expression region. However, a database containing health-associated reference expression intervals, health-associated reference expression regions, or instructions for determining inclusion in the regions can be conveniently accessed using appropriate hardware, software, and/or networking, for example, using hardware interfaced with networks, including the internet.

By using various hardware, software and network combinations, the methods of the invention can be conveniently performed in a variety of configurations. For example, a single computer apparatus can contain a comparative expression profiler, a database containing a collection of health-associated reference expression intervals for one or more molecules or one or more health-associated reference expression regions, and instructions for determining inclusion in one or more health-associated reference expression regions. Alternatively, the computer apparatus can contain a comparative expression profiler while the database of health-associated reference expression intervals or health-associated reference expression regions is stored on a separate medium. In addition, instructions for inclusion in one or more health-associated reference expression regions can be contained on a separate computer apparatus or separate medium, or combined with the computer apparatus containing the comparative expression profiler or the database on a separate medium. Such a separate medium can be another computer apparatus, a storage medium such as a floppy disk, Zip disk or a server such as a file-server, which can be accessed by a carrier wave such as an electromagnetic carrier wave. Thus, a computer apparatus containing a comparative expression profiler can remotely access a database, for example, a database stored on a file-server and accessible via a network such as the internet. One skilled in the art will know or can readily determine appropriate hardware, software or network interfaces that allow interconnection of an invention computer apparatus.

The invention also provides an apparatus comprising a comparative expression profiler and a means for determining the expression level of a molecule. Such a determining means can include a device which processes a specimen from an individual using the methods disclosed herein for determining the expression level of a molecule in a specimen. Such a device is one that can carry out the steps of contacting a specimen with a target and determining the expression level of a specimen molecule. The integration of a determining means with a comparative expression profiler in a single apparatus is particularly useful when a specimen is to be processed in a single location such as a diagnostic laboratory or physician's office.

A determining means and computer apparatus containing a comparative expression profiler can also be separate devices that are conveniently interfaced. For example, separate devices can be interfaced via a transportable medium, for example, a floppy disk, Zip disk, magnetic disk, external hard disk, and the like, which can be conveniently transferred from one device to the another. Alternatively, separate devices can be interfaced via a network. A network connection can be a physical linkage between the devices via a cable connection or can be connected via a carrier wave using any convenient combination of cables, servers, nodes, and the like, including connections via the internet or a similar network.

The use of separate devices for a determining means and a comparative expression profiler is particular useful for network applications that can be conveniently performed at a remote site. For example, a determining means can be a simple kit that contains an array of target ligands and appropriate buffers and reagents for processing a specimen to detect specimen molecules. Such a kit can be used, for example, in a clinical laboratory, a hospital, a physician's office, an ambulance, or even in the privacy of an individual's home.

Any of the methods, or portions thereof, disclosed herein can be adapted to a kit format for use in a remote location separate from a comparative expression profiler. For example, after exposing a component to a specimen in a remote location, the kit component exposed to the specimen can be forwarded to a clinical laboratory for analysis and determination of expression levels. Alternatively, the kit can contain components sufficient for determining the expression levels of specimen molecules at the remote location. After determining the expression levels of molecules in a specimen at a remote location, the information can be interfaced with a comparative expression profiler at a different location.

In the case of remote determination of expression levels, a simple interface between the determining means and a comparative expression profiler can be via a home or office computer. A convenient method to input expression levels from the determining means to a computer apparatus containing a comparative expression profiler can be by placing the determining means on a scanner, scanning the determining means array to convert the expression level of bound specimen molecules to an electronic output, and sending the scanned expression level information to a computer apparatus containing a comparative expression profiler via a network such as the internet. Using a scanner to detect expression levels of specimen molecules is particularly useful when the method of detection is a colorimetric signal. However, it is understood that any detection method suitable for detecting a specimen molecule can be adapted for remote use in a clinical laboratory, physician's office, or individual's home. For example, a hand held device incorporating suitable micro-detection systems, small scale assays, and other suitable methods for assaying samples on a small scale can optionally be used in remote detection of a specimen.

The invention further provides a computer-readable medium having stored thereon a plurality of sequences of instructions, the plurality of sequences of instructions including sequences of instructions which, when executed by a processor, cause the processor to perform the steps described above for execution on a computer apparatus. It is understood that any of the methods disclosed herein can be provided as an invention computer-readable medium. The invention additionally provides a carrier wave carrying instructions for a processor, the instructions which, when executed by the processor, cause the processor to perform the steps described above for execution on a computer apparatus. It is understood that any of the methods disclosed herein can be provided as an invention carrier wave.

Figure 6:
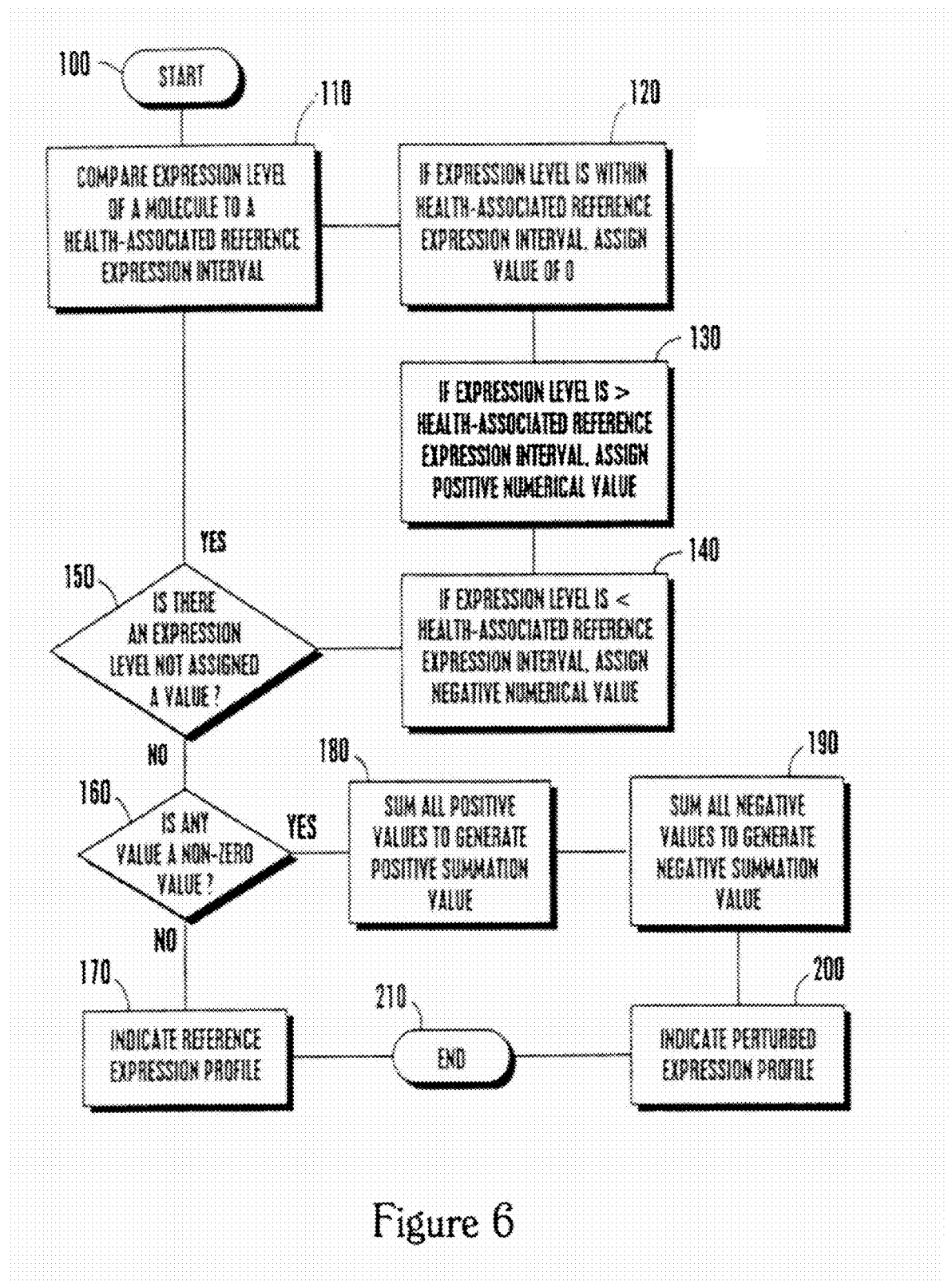
FIG. 6 shows a flow diagram that describes the operation of a method of determining a comparative expression profile one molecule at a time.

Referring to FIG. 6, a flow diagram that depicts the computer-executed steps of an embodiment of the invention is shown. Step 100 starts the implementation of an embodiment of the invention. In step 110, the expression level of a molecule is compared to a health-associated reference expression interval for that molecule. In step 120, a value of 0 is assigned if the expression level of the molecule is within the health-associated reference expression interval. In step 130, a positive numerical value is assigned if the expression level of the molecule is greater than a health-associated reference expression interval for that molecule. In step 140, a negative numerical value is assigned if the expression level of the molecule is less than a health-associated reference expression interval.

In step 150, an inquiry is performed to determine if there is a molecule having an expression level that is not assigned a value. If the answer is "yes," then step 110 is repeated for the molecule having an expression level that is not assigned a value. If the answer is "no," an inquiry is performed at step 160 to determine if any of the assigned values are non-zero values. If the answer is "no," a normal expression profile is indicated in step 170. If the answer is "yes," the positive values are summed to generate a positive summation value in step 180. In step 190, the negative values are summed to generate a negative summation value. In step 200, a perturbed expression profile is indicated. The method steps of determining a comparative expression profile end in step 210.

Figure 7:
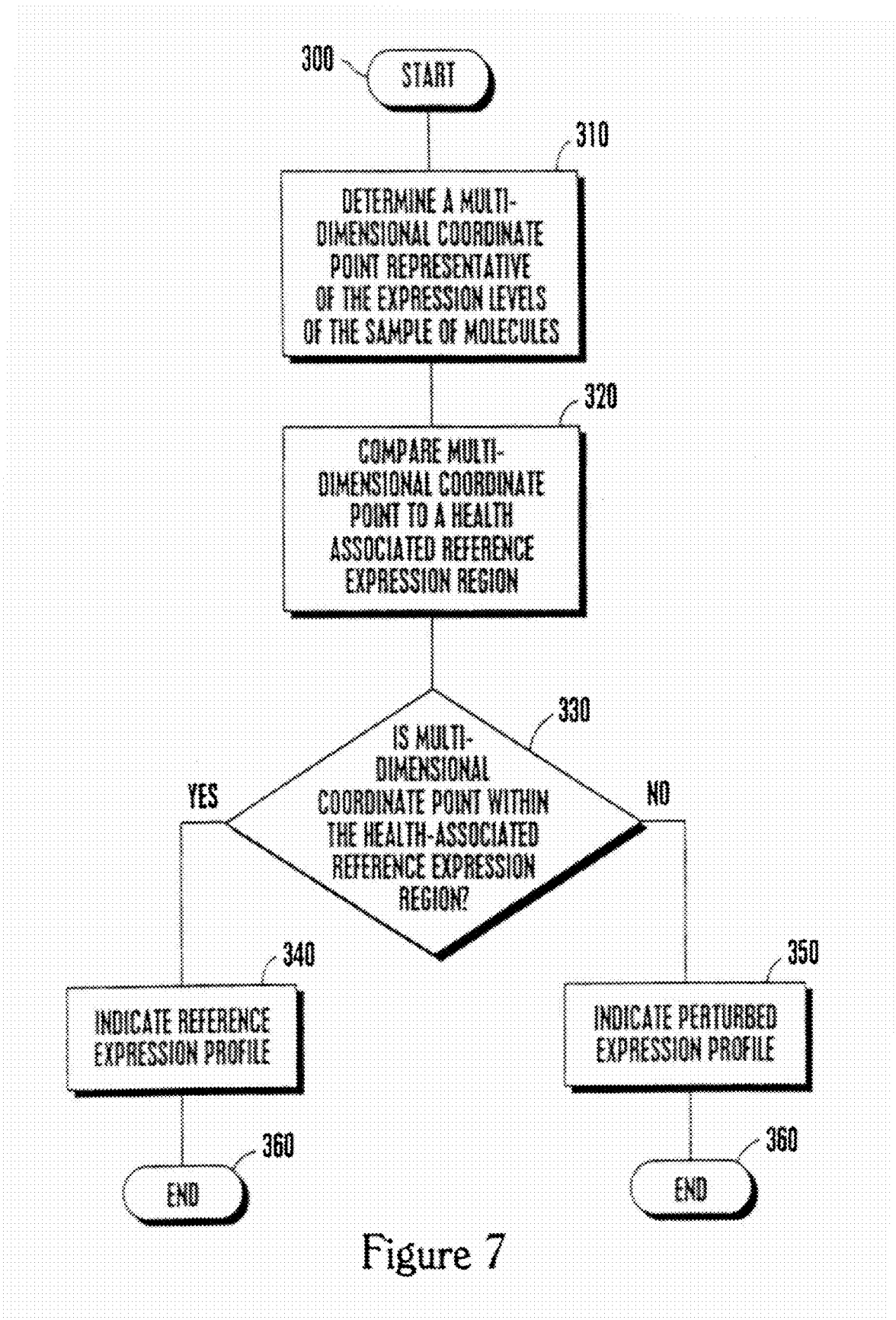
FIG. 7 shows a flow diagram that describes the operation of a method of determining a comparative expression profile in a multidimensional analysis.

Referring to FIG. 7, a flow diagram that depicts the computer-executed steps of an embodiment of the invention is shown. Step 300 starts the implementation of an embodiment of the invention. In step 310, a multidimensional coordinate point representative of the expression levels of the sample of molecules is determined. In step 320, the multidimensional coordinate point is compared to a health-associated reference expression region. In step 330, an inquiry is performed to determine if the multidimensional coordinate point is within the health-associated reference expression region. If the answer is "yes," a reference expression profile is indicated in step 340. If the answer is "no," a perturbed expression profile is indicated in step 350. The method steps of determining a comparative expression profile end in step 360. The expression levels of a sample of molecules determined separately can be inputted to determine a multidimensional coordinate point representative of the expression levels of the sample of molecules.

Figure 8:
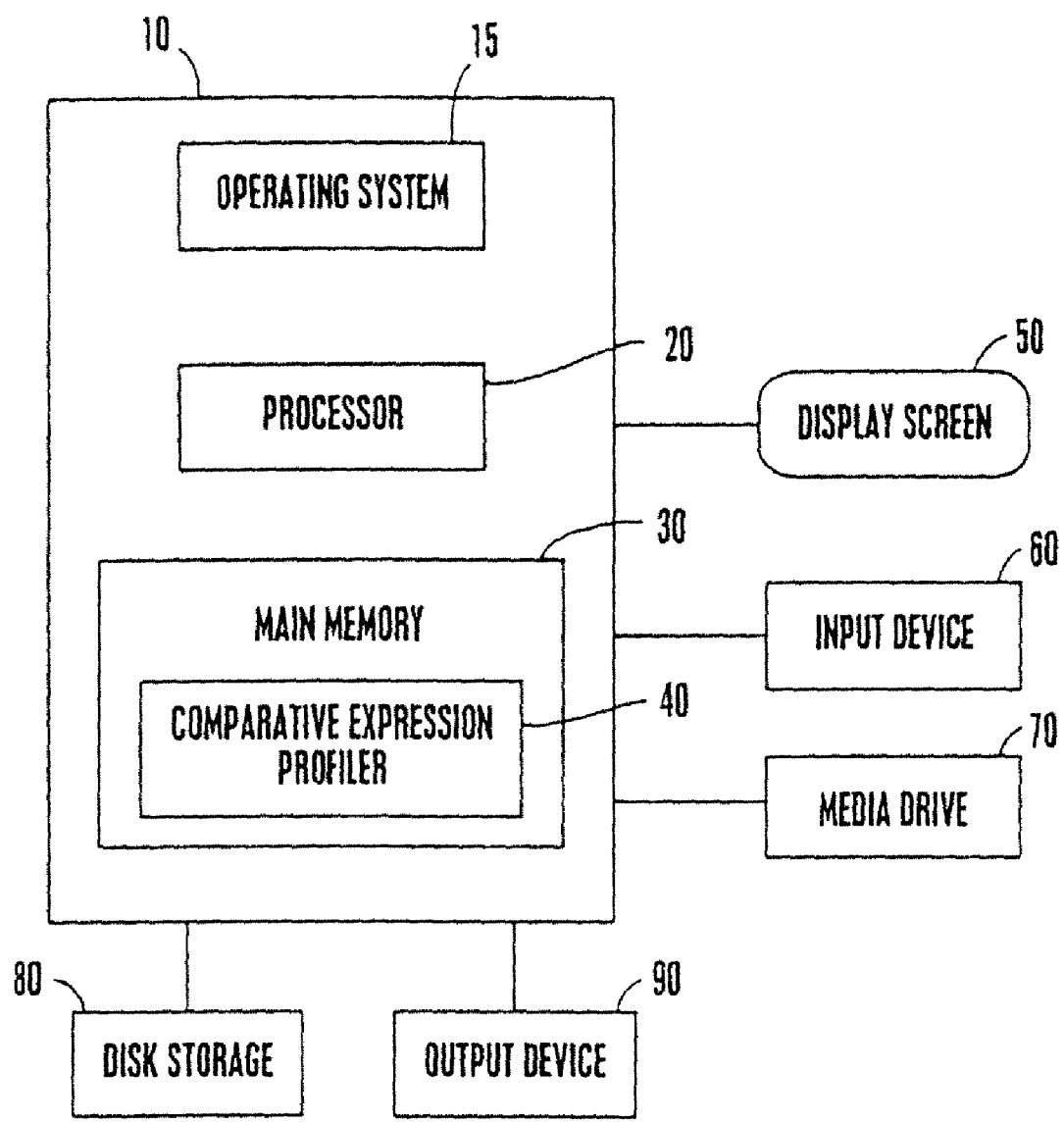
FIG. 8 shows a block diagram of a computer system containing a comparative expression profiler.

Referring to FIG. 8, a block diagram of computer system 10, which can be employed to implement the present invention, is shown. Computer system 10 has operating system 15, processor 20, main memory 30, comparative expression profiler 40, display screen 50, input device 60, media drive 70, disk storage 80, and output device 90, each of which is connected to system unit 10. Operating system 15 is an operating system such as UNIX, MS-DOS, Windows, or OS. The processor 20 is a general purpose programmable processor such as an Intel PENTIUM processor or a Motorola processor, suitable for a mid-size personal computer such as DEC, IBM, Macintosh and the like. The main memory 30 can be well known random access memory (RAM) that is sufficiently large to hold the necessary programming and data structures. The comparative expression profiler 40 in communication with main memory carries out computer-executable steps. For example, the comparative expression profiler can carry out the computer executable steps of comparing the expression level of a molecule with a health-associated reference expression interval for the molecule; and assigning a numerical value if the expression is within or outside a health-associated reference expression interval. The computer expression profiler can also carry out the computer executable steps of determining a multidimensional coordinate point representative of the expression levels of a sample of molecules from an individual; and comparing the multidimensional coordinate point with a health-associated reference expression region, wherein the multidimensional coordinate point within the health-associated reference expression region indicates a reference expression profile and wherein the multidimensional coordinate point outside the health-associated reference expression region indicates a perturbed expression profile.

The display screen 50 is a screen for visualizing, for example, input data. The input device 60 is a mouse or a keyboard, or a combination thereof, or any other device to input information. The media drive 70 is a drive, such as a tape drive, a disk drive or a CD drive, that provides the computer system 10 access to the comparative expression profiler 40.

The disk storage 80 is a device, such as a floppy disk, magnetic tape, Zip disk, external hard drive and the like that provides storage capacity for data. The output device 90 is a device such as a modem or portal that allows interfacing with a network.

It is understood that modifications which do not substantially affect the activity of the various embodiments of this invention are also provided within the definition of the invention provided herein. Accordingly, the following examples are intended to illustrate but not limit the present invention.

Example I

Calculation Methodology Using Multivariate Classification Theory

This example describes a calculation methodology using multivariate classification theory to classify health-associated regions of multidimensional space.

Data are available on expression levels corresponding to a set of molecules for individuals with known health states, for example, healthy, ovarian cancer, prostate cancer, diabetes, and the like. The number m corresponds to the number of different health states. The calculation steps involved are: (1) estimate the probability distribution of the observed data vector for each health state; (2) estimate the costs of misclassification for each combination of health states; (3) estimate the a priori probabilities of a random individual being a member of each health state; and (4) determine the optimal calculation to be performed when classifying a new individual. The development given here is based upon multivariate statistical methods such as those of T. W. Anderson (*An Introduction to Multivariate Statistical Analysis*, Second Edition, Wiley, N.Y., 1984, Section 6.7).

(1) Estimation of the Probability Distribution of the Data for a Given Health State The estimated probability density function for a vector x of molecular expression levels for health state i is denoted by $p_i(x)$. Many methods are available for this purpose. For example, a model can assume that the distribution is multivariate normal and use the sample average expression level for each molecule (averaged over individuals known to be in the given health state) and the sample covariance matrix of expression levels as estimates of the mean vector and covariance matrix of the multivariate normal distribution specifying the data distribution for this health state. Exploratory data analysis can be used to determine whether the multivariate normal assumption is appropriate. Alternatives such as mixture distributions, multivariate t distributions, transformation or kernel smoothing techniques can also be used.

(2) Estimation of the Costs of Misclassification

Costs are denoted $C(j|i)$ representing the cost of misclassifying an individual as health state j when he or she actually is in health state i (where $i,j=1, \ldots, m$). Complete flexibility is allowed in the setting of relative costs of misclassification in that a different cost figure can be set for each combination of health states. Thus, the cost of misclassifying a healthy individual as cancerous can be set either to be the same or different from the cost of classifying a cancerous individual as healthy. With m health states, costs can be specified for $m(m-1)$ combinations of health states. One available choice of costs is to set them all equal to 1, which says that any and all misclassifications are equally costly.

(3) Estimation of the a Priori Probabilities of Health States

Epidemiological data on the incidence of each disease in the general population or a specific population can be used to estimate these a priori probabilities for the health states, which will be denoted $q_1, q_2, \ldots, q_m$.

(4) The Optimal Calculation for Classifying a New Individual

In order to minimize the expected cost, averaged over many individuals classified by the system, the optimal decision rule is as follows. A new individual with expression levels specified by a vector x for a set of molecules is classified as being in health state k if $$\sum_{\substack{i=1 \\ i \neq k}}^{m} q_i p_i(x) C(k|i) < \sum_{\substack{i=1 \\ i \neq j}}^{m} q_i p_i(x) C(j|i),$$

$$j = 1, \ldots, m, j \neq k$$

This is the calculation that determines the health-associated reference region containing the vector x.

Figure 3:
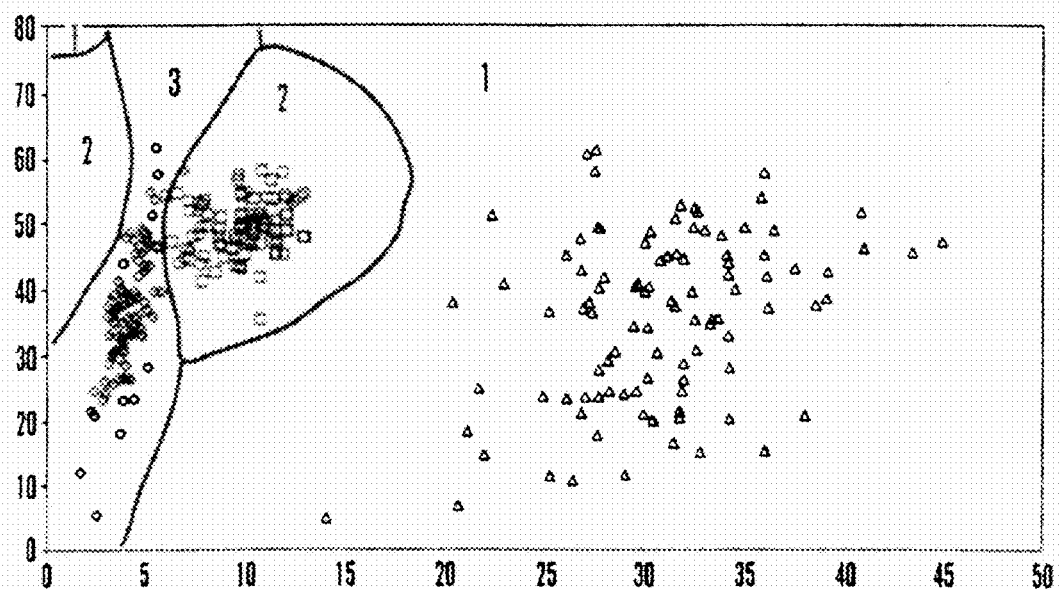
FIG. 3 shows the coordinate points in two-dimensional space representative of the expression levels (in arbitrary units) of two molecules. The data set shows three health states that can be classified in three regions, corresponding to three health-associated reference expression regions.

For the data set shown in FIG. 3 for three health states and two molecular expression levels, the resulting classification regions are shown under the assumptions that each of the three populations is bivariate normal, the costs of misclassification are all equal, and the prior probabilities are 0.7, 0.2, and 0.1 for the three groups. Because health state 3 is rare, the optimal classification scheme reverts to the more common (and more disperse) health states 1 and 2 at the upper left.

This example demonstrates that a statistical classification method can be applied to multiple parameters in a two-dimensional analysis to classify three distinct health states corresponding to health-associated reference regions for three populations of individuals.

Example II

Logistic Regression Analysis

This example describes the analysis of a data set for three health states and two molecular expression levels using logistic regression analysis.

Figure 4A:
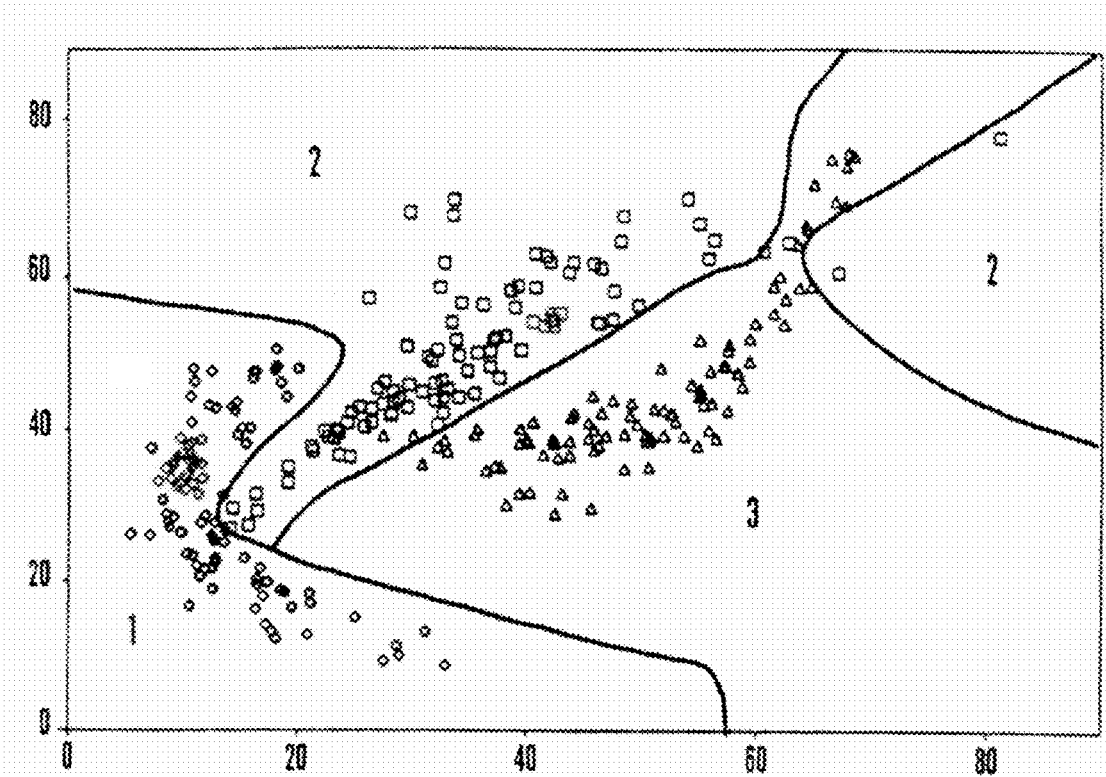
FIGS. 4A and B shows a data set for three health states and two molecular expression levels determined by logistic regression analysis, with FIG. 4B showing the coordinates of individuals "A" (x) and "B" (+).

The data set was created starting with pseudorandom computer-generated numbers and then applying a different mathematical transformation for each health related reference group. For the data set shown in FIG. 4A for three health states and two molecular expression levels, the resulting classification regions are shown using logistic regression analysis under the assumptions that the costs of misclassification are all equal, and the prior probabilities are 0.2, 0.5, and 0.3 for the three groups. Because health state 2 is the most common in the population, the classification tends to favor this group at the upper right where data are sparse.

The classification regions are based on three separate logistic regression analyses, one to predict each health state, where each analysis used the molecular expression levels for all health states but coded the independent variable to indicate the health state to be predicted. To allow for the curvature in the data, the predictor variables were chosen to be cubic polynomials in the predictor variables with a backward stepwise selection process to omit terms that do not contribute to the prediction. The resulting predicted probability for each health state can be scaled by its prior probability of occurrence in the population, and the resulting scores compared. The health state with the largest score is the chosen classification, while the relative values of all three scores indicate the relative likelihoods of the three health states.

The assignment of new individuals "A" and "B" to one of the three defined health states were determined. The molecular expression levels of two new individuals "A" and "B", with unknown health states, are shown in FIG. 4B, with A indicated as "×" and B indicated as "+."

The following method was used for computing the degree of confidence in the assignment of a new individual: (a) compute the predicted probability for each health state using the results of the logistic regression analyses (where these results do not include the new individual) evaluated at the expression levels for the new individual; (b) multiply each of these numbers by the prior probability of that health state occurring in the population; (c) divide each of the three resulting numbers by their sum in order to convert them into probabilities that add up to 1. The results of these steps are the relative probabilities that the new individual belongs to each health group.

Figure 4B:
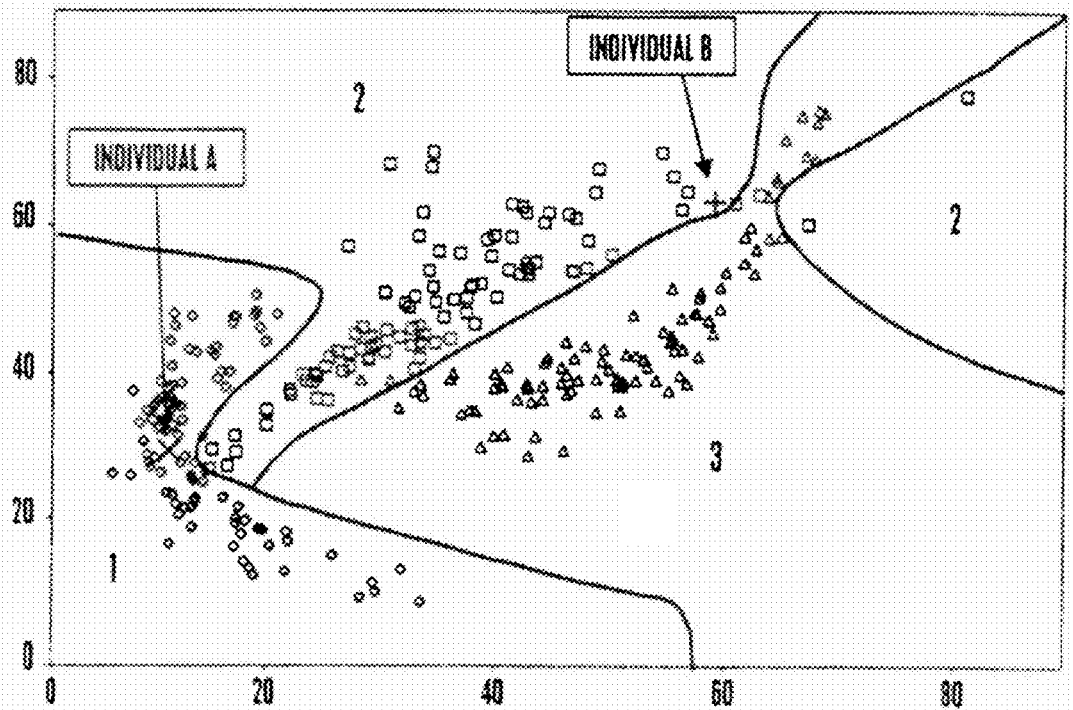

The degree of confidence in the assignment of individual A to health group 1 was assessed by examining the relative probabilities of individual A belonging to each health group, and the results were consistent with FIG. 4B, which shows that individual A is clearly well-described as being within the data for individuals with health state 1. The results show that individual A has a 97.0% chance of being in health state 1, a 2.8% chance of being in health state 2, and a 0.2% chance of being in health state 3, as predicted using the model.

Individual B was also assigned to a health state, although the degree of confidence was less than for individual A. The degree of confidence in the assignment of individual B to health group 2 was assessed, and the results are consistent with FIG. 4B, which shows that individual B is near the boundary that separates individuals with health state 2 from those having health state 3. The results show that individual B has a 2.1% chance of being in health state 1, a 74.2% chance of being in health state 2, and a 23.6% chance of being in health state 3, as predicted using the model.

This example shows that logistic regression analysis can be used classify the health states of a group of reference individuals and the assignment of an individual to a reference health state.

Example III

Machine Learning by Boosting of Individual Molecules

This example describes classification analysis using a machine learning algorithm called "boosting" to combine a chosen group of simple one-molecule-at-a-time decision rules to obtain an effective health classification.

Figure 5:
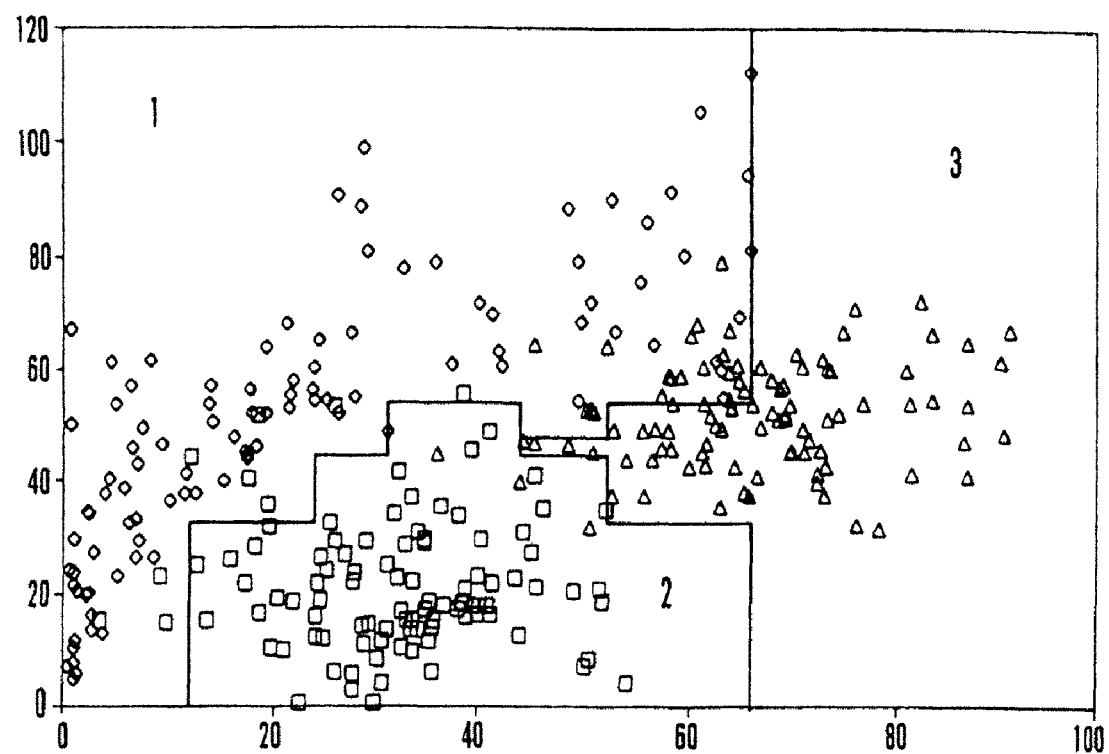
FIG. 5 shows a data set for three health states and two expression levels determined by machine learning by boosting of individual molecules.

The data set was created starting with pseudorandom computer-generated numbers and then applying a different mathematical transformation for each health related reference group. For the data set shown in FIG. 5 for three health states and two molecular expression levels, the resulting classification regions are shown for a machine-learning technique that uses boosting to combine several one-molecule-at-a-time analyses to form a classification region under the assumption that the prior probabilities are 0.6, 0.3, and 0.1 for the three groups. In this case, 8 boosting steps have been taken. The method used here is based on the AdaBoost.M1 algorithm described by Freund and Schapire (*J. Computer and System Sciences*, 55:119-139 (1997)).

The boosting technique in machine learning generally relies on a set of simple "weak learners" that are trained on the data with successive weightings to give more importance to initial misclassifications in an effort to improve the results. By selecting a set of weak learners and letting them vote on the most likely classification, the boosting technique is able to create a consensus decision rule that is much stronger than any individual weak learner.

In this example, the weak learners are simple decision rules based on one-molecule-at-a-time analysis in which a molecule is chosen (in this case, either molecule 1 or molecule 2), and then two threshold values a and b are chosen with $a \leq b$. An ordering of the health states 1, 2, and 3, which can be perumted, is also specified, perhaps 2, 3, 1. The decision rule corresponding to these threshold values and this ordering of health states would decide on health state 2 if the molecular expression level of this molecule is less than or equal to a, would decide on health state 3 if the molecular expression level is between a and b, and would decide health state 1 if the expression level is at least b.

Once the weak learners have been specified, the AdaBoost.M1 algorithm (Freund and Schapire, supra, 1997) operates automatically, as follows.

(a) Define weights w(i) to represent the initial, prior probabilities for the given data indexed by i.
(b) Loop as t goes from 1 to T, where T is the number of boosting iterations to be used.
  (b.1) Define probabilities p(i) equal to w(i) divided by the sum of the w(i) so that $p(i)=w(i)/\Sigma w(j)$. Note that these weights and probabilities will change as the algorithm proceeds.
  (b.2) Find the optimal weak learner that minimizes the expected error rate with respect to the current probabilities, where the error rate of a weak learner is defined as the sum of the p(i) for those observations that are misclassified by the weak learner.
  (b.3) If this optimal weak learner has an error rate larger than 0.5, then set t equal to t−1 and stop.
  (b.4) Define $\beta(t)=bestError/(1-bestError)$ using the error rate for the optimal weak learner using the error rate calculation as specified in step (b.2), that is, bestError refers to the error rate computed using the definition of step (b.2).
  (b.5) Update the weights by replacing w(i) with $\beta(t) \times w(i)$ for those observations i that were classified correctly. This has the effect of downweighting those observations that were correctly classified.
(c) Weak learners t have now been selected, where t=T, unless the method is stopped early due to error rate >0.5.
(d) To assign a classification to a new observation, first note that each of the t selected weak learners assigns a health state to the new observation, although individual weak learners can assign different health states. These t weak learners are allowed to vote, giving weak learner k weight $\ln(1/\beta(k))$. The health state receiving the largest total weight from the selected weak learners is the assigned classification.

This example shows that machine learning by boosting of individual molecules can be used classify the health states of a group of reference individuals.

Throughout this application various publications have been referenced. The disclosures of these publications in their entireties are hereby incorporated by reference in this application in order to more fully describe the state of the art to which this invention pertains.

Although the invention has been described above, it should be understood that various modifications can be made without departing from the spirit of the invention. Accordingly, the invention is limited only by the claims.

What is claimed is:

1. A method of determining whether an individual has an expression profile that indicates health, or an expression profile that indicates disease condition, comprising measuring the expression levels of the plurality of molecules in a specimen from said individual, and assessing whether the expression levels of a plurality of molecules in said specimen fall within health-associated reference expression regions for said plurality of molecules, wherein expression levels within said health-associated reference expression regions indicate health and wherein expression levels outside said health-associated reference expression regions indicate disease condition.

2. The method of claim 1, wherein said specimen is leukocytes, blood, or serum.

3. The method of claim 1, wherein said expression levels are measured as levels of mRNA.

4. The method of claim 3, wherein said specimen is contacted with an array of nucleic acid probes.

5. The method of claim 1, wherein said expression levels are measured as levels of polypeptides.

6. The method of claim 5, wherein said specimen is contacted with an array of antibodies.

7. The method of claim 1, wherein said expression levels are measured as levels of small molecules.

8. A computer-readable storage medium having stored thereon a plurality of sequences of instructions, which, when executed by a processor, cause said processor to perform the steps of:

(a) determining whether the expression level of a molecule is within a health-associated reference expression region of said molecule; and (b) assigning a value of 0 if said expression level is within said health-associated reference expression region, assigning a positive numerical value if said expression level is greater than said health-associated reference expression region, or assigning a negative numerical value if said expression level is less than said health-associated reference expression region.

* * * * *